US012652878B2

(12) United States Patent
Tojinbara

(10) Patent No.: US 12,652,878 B2
(45) Date of Patent: Jun. 9, 2026

(54) IMAGING DEVICE AND ELECTRONIC APPARATUS

(71) Applicant: SONY SEMICONDUCTOR SOLUTIONS CORPORATION, Kanagawa (JP)

(72) Inventor: Hiroki Tojinbara, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 130 days.

(21) Appl. No.: 18/629,265

(22) Filed: Apr. 8, 2024

(65) Prior Publication Data

US 2024/0258356 A1     Aug. 1, 2024

Related U.S. Application Data

(63) Continuation of application No. 17/775,850, filed as application No. PCT/JP2020/043142 on Nov. 19, 2020, now Pat. No. 11,973,102.

(30) Foreign Application Priority Data

Nov. 29, 2019     (JP) ................................. 2019-216511

(51) Int. Cl.
*H10F 39/00*        (2025.01)
*A61B 1/05*        (2006.01)
                (Continued)

(52) U.S. Cl.
CPC ........... *H10F 39/811* (2025.01); *H04N 25/77* (2023.01); *H04N 25/7795* (2023.01);
                (Continued)

(58) Field of Classification Search
CPC ........ H04N 25/79; H04N 25/75; H04N 25/77; H04N 25/78; H01L 24/08;
                (Continued)

(56) References Cited

U.S. PATENT DOCUMENTS 8,878,267 B2    11/2014  Inui
9,888,197 B1 *   2/2018  Hynecek ............... H10F 39/199
                (Continued)

FOREIGN PATENT DOCUMENTS

CN        101753866 A      6/2010
CN        102124566 A      7/2011
                (Continued)

OTHER PUBLICATIONS

International Search Report and Written Opinion for International (PCT) Patent Application No. PCT/JP2020/043142, dated Feb. 2, 2021, 7 pages.
                (Continued)

*Primary Examiner* — Pritham D Prabhakher
(74) *Attorney, Agent, or Firm* — SHERIDAN ROSS P.C.

(57)                ABSTRACT

An imaging device including: a first semiconductor substrate; a second semiconductor substrate; and a wiring layer. The first semiconductor substrate has a first surface and a second surface and includes a sensor pixel. The second semiconductor substrate has a third surface and a fourth surface and includes a readout circuit that outputs a pixel signal based on an output from the sensor pixel. The second semiconductor substrate is stacked on the first semiconductor substrate with the first surface and the fourth surface opposed to each other. The wiring layer is between the first semiconductor substrate and the second semiconductor substrate and includes a first wiring line and a second wiring line that are electrically coupled to each other. One of the first wiring line and the second wiring line is in an electrically floating state while the other is electrically coupled to a transistor.

20 Claims, 16 Drawing Sheets

(51) Int. Cl.

| | |
|---|---|
| *H01L 23/00* | (2006.01) |
| *H04N 25/76* | (2023.01) |
| *H04N 25/77* | (2023.01) |
| *H04N 25/78* | (2023.01) |
| *H04N 25/79* | (2023.01) |
| *H10F 39/18* | (2025.01) |
| *H10W 90/00* | (2026.01) |

(52) U.S. Cl.

CPC ............. *H04N 25/78* (2023.01); *H04N 25/79* (2023.01); *H10F 39/809* (2025.01); *A61B 1/05* (2013.01); *H10F 39/184* (2025.01); *H10W 90/792* (2026.01)

(58) Field of Classification Search

CPC ........ H01L 27/14634; H01L 27/14636; H01L 27/14609; H01L 27/14638; H01L 27/14649; H01L 27/14603; H01L 27/14641; H01L 2224/08147; A61B 1/05

USPC ........................................ 348/294

See application file for complete search history.

(56) References Cited

U.S. PATENT DOCUMENTS

| | | | | |
|---|---|---|---|---|
| 10,171,760 | B2 * | 1/2019 | Otaka | H04N 25/77 |
| 10,332,928 | B2 * | 6/2019 | Mori | H10F 39/014 |
| 10,396,116 | B2 * | 8/2019 | Tanaka | H10F 39/811 |
| 10,446,594 | B2 | 10/2019 | Tashiro et al. | |
| 10,630,916 | B2 * | 4/2020 | Kaibara | H04N 25/42 |
| 10,659,705 | B2 * | 5/2020 | Sano | H04N 25/625 |
| 10,764,520 | B2 | 9/2020 | Onuki et al. | |
| 10,848,695 | B2 | 11/2020 | Miki et al. | |
| 10,917,602 | B2 * | 2/2021 | Tsukuda | H04N 25/79 |
| 11,108,985 | B2 * | 8/2021 | Nakamura | H04N 25/618 |
| 11,205,669 | B2 | 12/2021 | Okamoto et al. | |
| 2010/0060764 | A1 | 3/2010 | Mccarten | |
| 2010/0238331 | A1 | 9/2010 | Umebayashi et al. | |
| 2014/0022427 | A1 | 1/2014 | Goto et al. | |
| 2015/0319369 | A1 * | 11/2015 | Serrano Gotarredona | H04N 25/778 250/208.1 |
| 2015/0372043 | A1 | 12/2015 | Sano et al. | |
| 2017/0092670 | A1 | 3/2017 | Okamoto et al. | |
| 2018/0047767 | A1 | 2/2018 | Ando | |
| 2018/0054576 | A1 * | 2/2018 | Otaka | H04N 25/78 |
| 2018/0213169 | A1 | 7/2018 | Onuki et al. | |
| 2018/0240834 | A1 * | 8/2018 | Tanaka | H10F 39/811 |
| 2018/0247969 | A1 * | 8/2018 | Mori | H04N 25/59 |
| 2018/0295303 | A1 * | 10/2018 | Murao | H10F 39/809 |
| 2018/0324371 | A1 * | 11/2018 | Sano | H04N 25/625 |
| 2018/0376093 | A1 * | 12/2018 | Tsukuda | H04N 25/79 |
| 2019/0104266 | A1 * | 4/2019 | Murata | H04N 25/7795 |
| 2019/0174080 | A1 | 6/2019 | Kaibara | |
| 2019/0253653 | A1 * | 8/2019 | Nakamura | H04N 25/69 |
| 2019/0253659 | A1 | 8/2019 | Kobayashi et al. | |
| 2019/0268554 | A1 | 8/2019 | Kawai | |
| 2020/0035736 | A1 | 1/2020 | Nagahama | |
| 2020/0135786 | A1 * | 4/2020 | Onuki | H10F 39/8037 |
| 2020/0235151 | A1 | 7/2020 | Suzuki et al. | |
| 2021/0020857 | A1 | 1/2021 | Hirata et al. | |
| 2022/0392942 | A1 | 12/2022 | Tojinbara | |

FOREIGN PATENT DOCUMENTS

| | | |
|---|---|---|
| CN | 102623463 A | 8/2012 |
| CN | 103745983 A | 4/2014 |
| CN | 107408565 A | 11/2017 |
| CN | 110447105 A | 11/2019 |
| CN | 110494962 A | 11/2019 |
| EP | 2324506 | 5/2011 |
| JP | 2004063859 A | 2/2004 |
| JP | 2011-166170 | 8/2011 |
| JP | 2012-147169 | 8/2012 |
| JP | 2014-022561 | 2/2014 |
| JP | 2018206837 A | 12/2018 |
| KR | 20110050670 A | 5/2011 |
| TW | 201903971 A | 1/2019 |
| WO | WO-2015016140 A1 | 2/2015 |
| WO | WO 2017/043343 | 3/2017 |
| WO | WO 2018/186026 | 10/2018 |
| WO | WO-2018216442 A1 | 11/2018 |
| WO | WO-2019130702 A1 | 7/2019 |
| WO | WO-2019225250 A1 | 11/2019 |

OTHER PUBLICATIONS

Notice of Allowance for U.S. Appl. No. 17/775,850, dated Jan. 4, 2024, 15 pages.

Zhou Xin, et al., "Research of Active Pixel Structure Based on Standard CMOS Technology", Piezoelectrics & Acoust Ooptics, vol. 27 No. 4, Aug. 25, 2005.

* cited by examiner

IMAGING DEVICE AND ELECTRONIC APPARATUS

CROSS REFERENCE TO RELATED APPLICATIONS

This application is a continuation of U.S. patent application Ser. No. 17/775,850, filed May 10, 2022, which is a national stage application under 35 U.S.C. 371 and claims the benefit of PCT Application No. PCT/JP2020/043142, having an international filing date of Nov. 19, 2020, which designated the United States, which PCT application claimed the benefit of Japanese Patent Application No. 2019-216511, filed Nov. 29, 2019, the entire disclosures of each of which are incorporated herein by reference.

TECHNICAL FIELD

The present disclosure relates to an imaging device having a three-dimensional structure and an electronic apparatus including the imaging device.

BACKGROUND ART

The introduction of a miniaturization process and an increase in packaging density have decreased the area of one pixel in an imaging device having a two-dimensional structure. In recent years, to achieve a further smaller imaging devices and higher pixel density, imaging devices have been developed that each have a three-dimensional structure. In an imaging device having a three-dimensional structure, for example, a semiconductor substrate including a plurality of sensor pixels and a semiconductor substrate including a signal processing circuit are stacked (see, for example, PTL 1). The signal processing circuit processes a signal obtained by each of the sensor pixels.

CITATION LIST

Patent Literature

PTL 1: Japanese Unexamined Patent Application Publication No. 2014-22561

SUMMARY OF THE INVENTION

Incidentally, an imaging device having a three-dimensional structure is requested to have an extended dynamic range.

It is desirable to provide an imaging device and an electronic apparatus that make it possible to extend the dynamic range.

An imaging device according to an embodiment of the present disclosure includes: a first semiconductor substrate; a second semiconductor substrate; and a wiring layer. The first semiconductor substrate has a first surface and a second surface and includes a sensor pixel that performs photoelectric conversion. The second semiconductor substrate has a third surface and a fourth surface and includes a readout circuit that outputs a pixel signal based on electric charge outputted from the sensor pixel. The second semiconductor substrate is stacked on the first semiconductor substrate with the first surface and the fourth surface opposed to each other. The wiring layer is provided between the first semiconductor substrate and the second semiconductor substrate and includes a first wiring line and a second wiring line that are electrically coupled to each other. One of the first wiring line and the second wiring line is in an electrically floating state while another of the first wiring line and the second wiring line is electrically coupled to a transistor provided to the first semiconductor substrate or the second semiconductor substrate.

An electronic apparatus according to an embodiment of the present disclosure includes the imaging device according to the embodiment of the present disclosure described above.

In the imaging device according to the embodiment of the present disclosure and the electronic apparatus according to the embodiment, the first wiring line and the second wiring line are provided inside the wiring layers formed on the respective opposed surfaces of the first semiconductor substrate including the sensor pixel and the second semiconductor substrate including the readout circuit. This increases the wiring capacitance. One of the first wiring line and the second wiring line is in the electrically floating state. The other of the first wiring line and the second wiring line is electrically coupled to the transistor provided to the first semiconductor substrate or the second semiconductor substrate. The first wiring line and the second wiring line are electrically coupled to each other.

MODES FOR CARRYING OUT THE INVENTION

The following describes an embodiment of the present disclosure in detail with reference to the drawings. The following description is a specific example of the present disclosure, but the present disclosure is not limited to the following modes. In addition, the present disclosure is not also limited to the disposition, dimensions, dimension ratios, and the like of the respective components illustrated in the respective diagrams. It is to be noted that description is given in the following order.

1. First Embodiment (Example of an imaging device in which an additional capacitance wiring line is provided in a first substrate and a second substrate)
1-1. Schematic Configuration of Imaging Device
1-2. Specific Configuration of Imaging Device
1-3. Workings and Effects
2. Modification Example 1
3. Second Embodiment (Example of an imaging device in which three substrates are stacked)
4. Modification Example 2
5. Application Example
6. Practical Application Examples

1. FIRST EMBODIMENT

1-1. Schematic Configuration of Imaging Device

Figure 1:
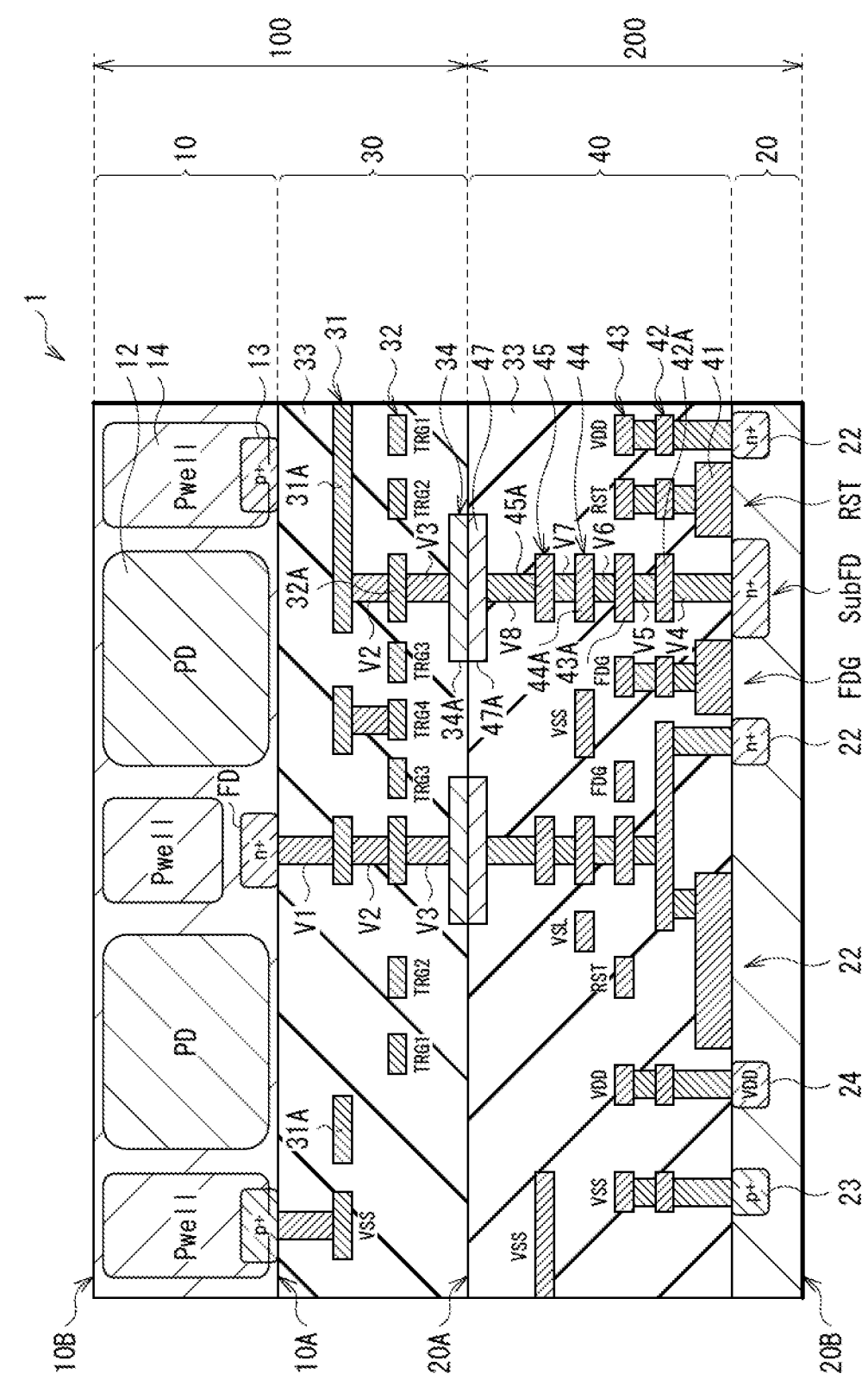
FIG. 1 is a cross-sectional schematic diagram illustrating a configuration of an imaging device according to a first embodiment of the present disclosure in a vertical direction.
Figure 2:
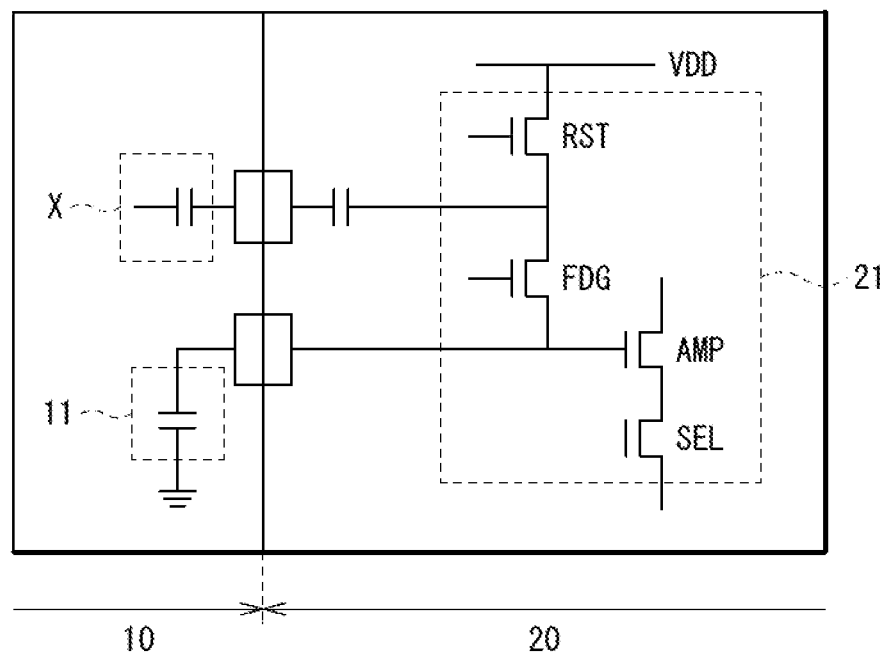
FIG. 2 is a diagram illustrating an example of an equivalent circuit of the imaging device illustrated in FIG. 1.
Figure 3:
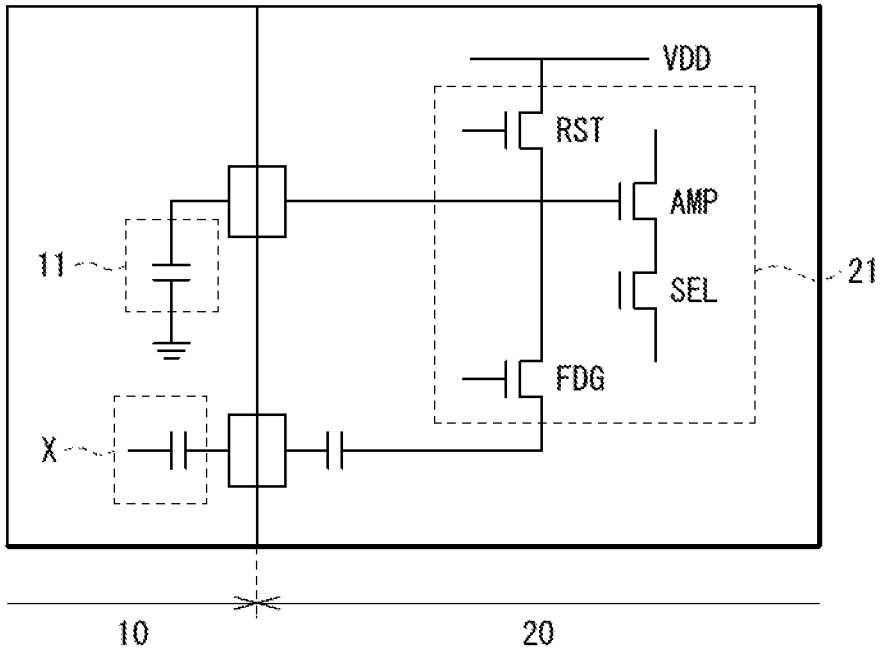
FIG. 3 is a diagram illustrating another example of the equivalent circuit of the imaging device illustrated in FIG. 1.
Figure 4:
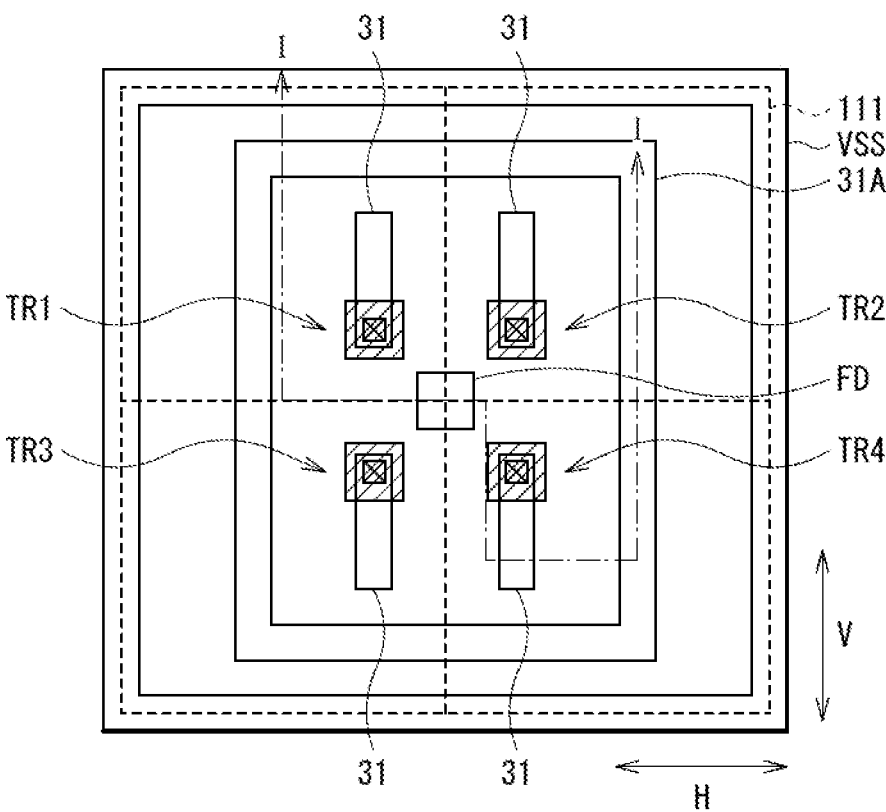
FIG. 4 is a schematic diagram illustrating an example of a layout of a gate wiring line and a lower wiring layer in a first substrate illustrated in FIG. 1.
Figure 5:
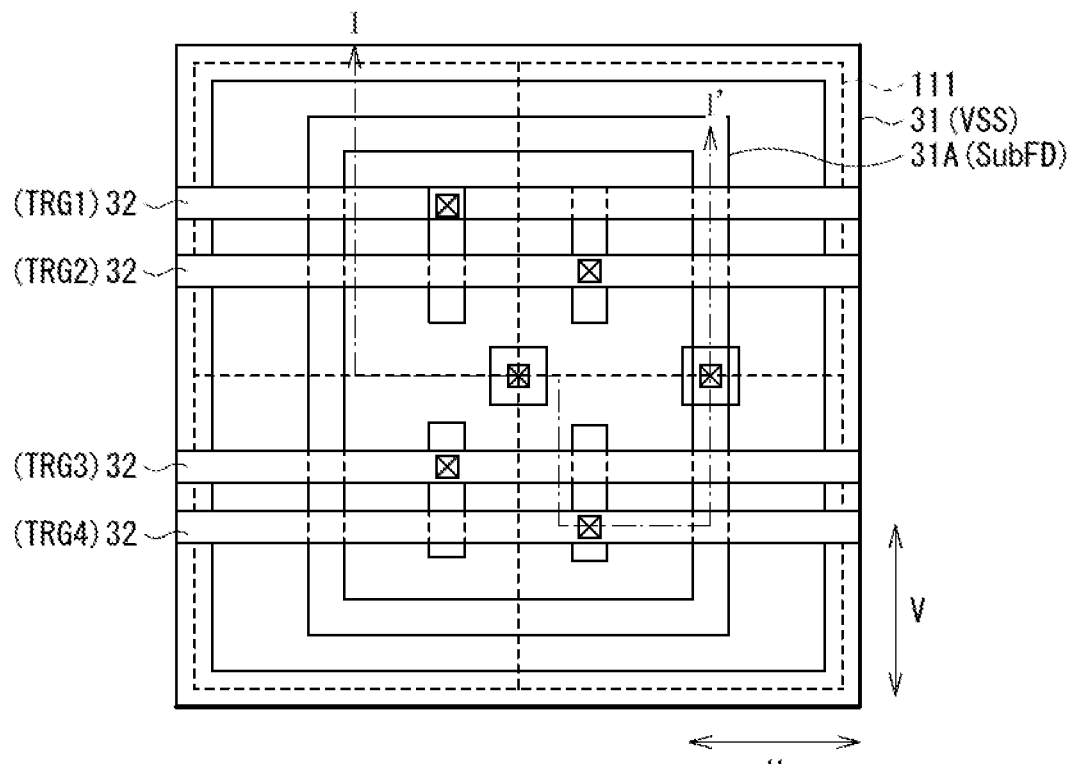
FIG. 5 is a schematic diagram illustrating an example of a wiring layout of the lower wiring layer and an upper wiring layer in the first substrate illustrated in FIG. 1.
Figure 6:
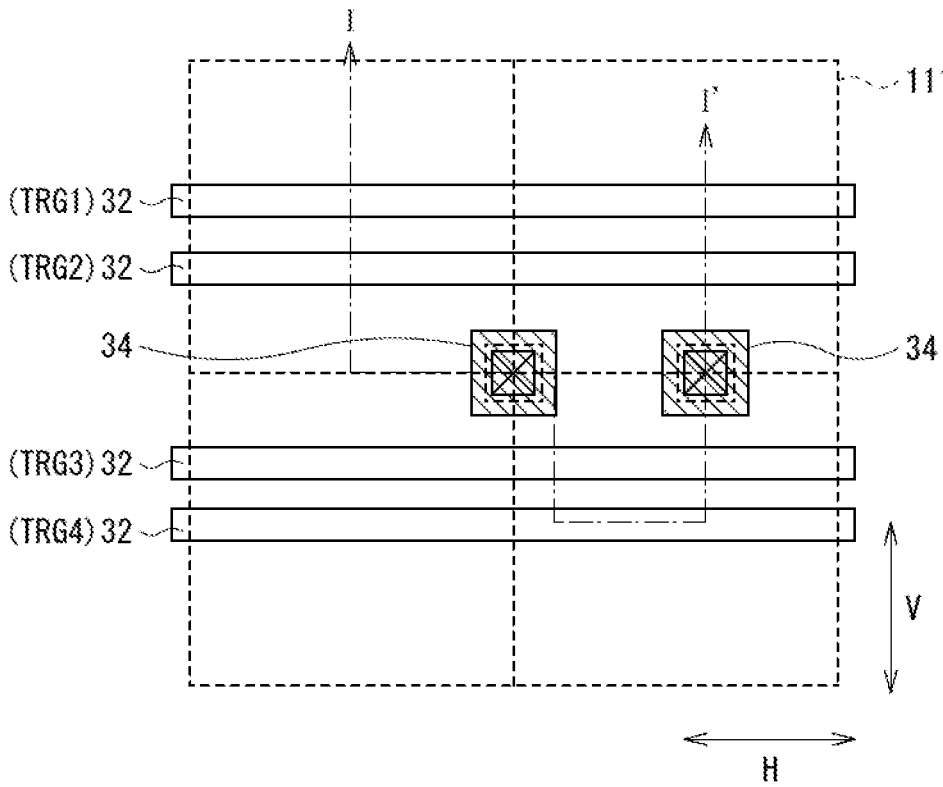
FIG. 6 is a schematic diagram illustrating an example of a wiring layout of the upper wiring layer and a pad electrode in the first substrate illustrated in FIG. 1.
Figure 7:
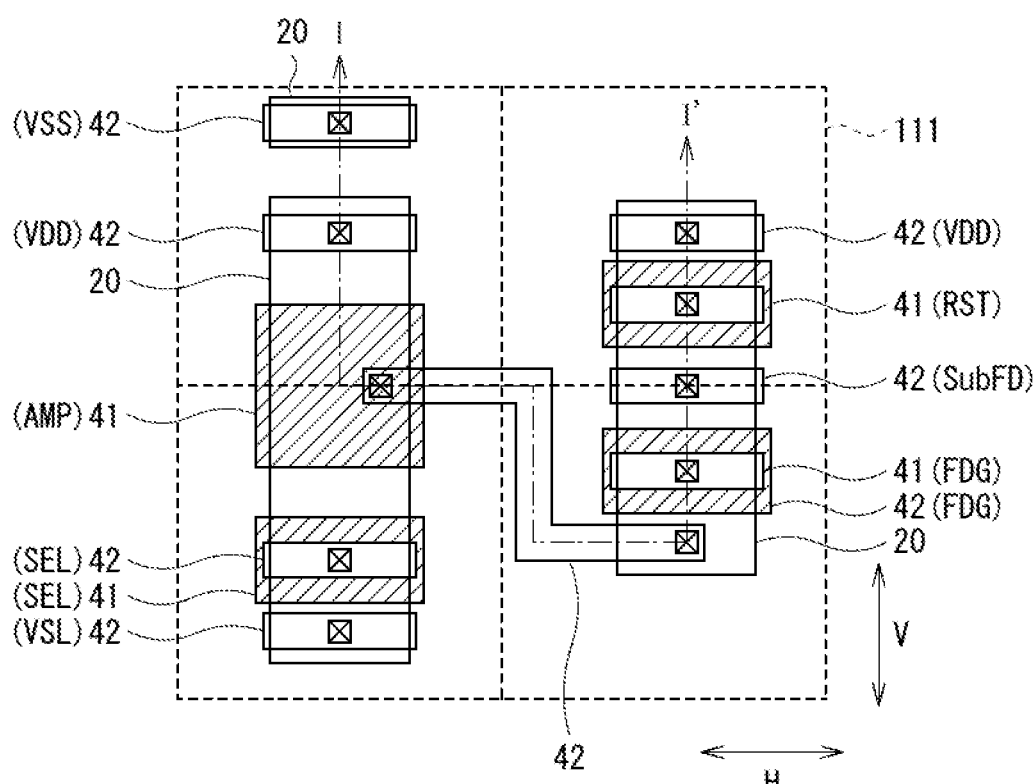
FIG. 7 is a schematic diagram illustrating an example of a layout of a gate wiring line and a lower wiring layer in a second substrate illustrated in FIG. 1.
Figure 8:
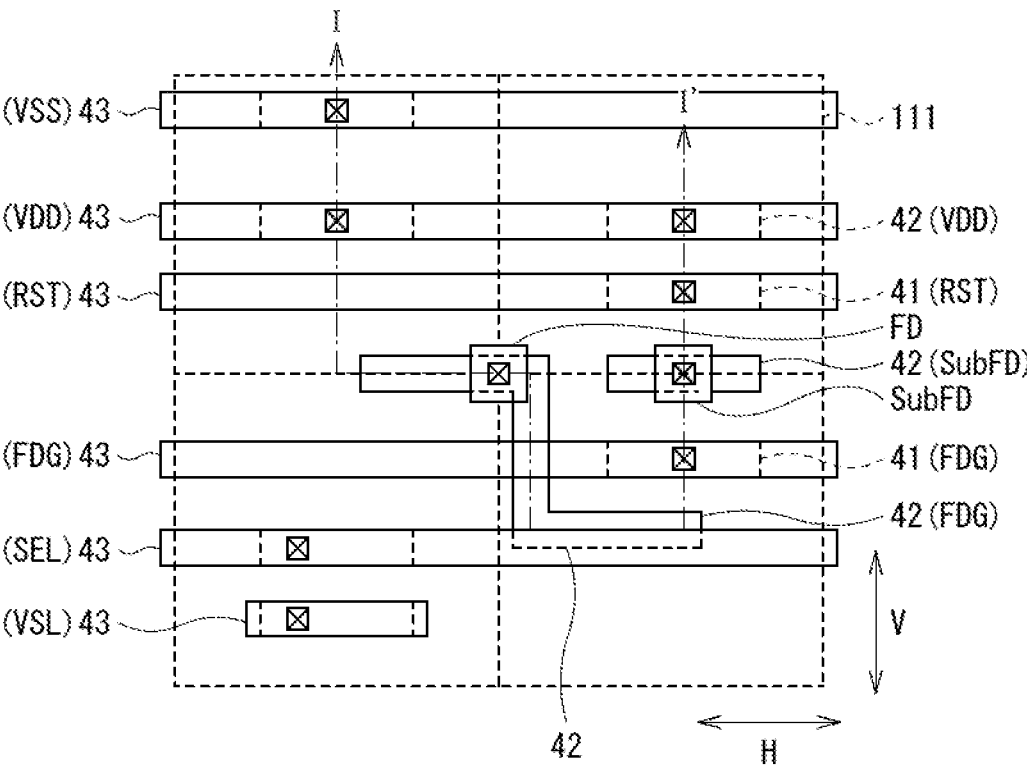
FIG. 8 is a schematic diagram illustrating an example of a wiring layout of the lower wiring layer and a first intermediate wiring layer in the second substrate illustrated in FIG. 1.
Figure 9:
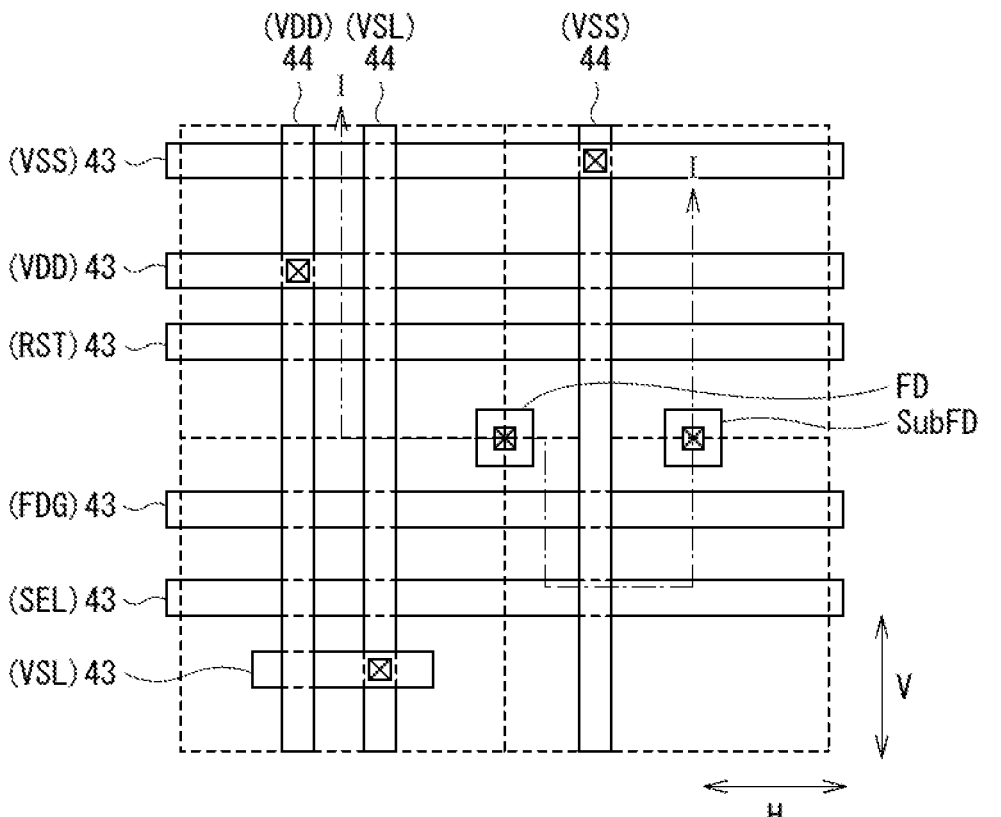
FIG. 9 is a schematic diagram illustrating an example of a wiring layout of the first intermediate wiring layer and a second intermediate wiring layer in the second substrate illustrated in FIG. 1.
Figure 10:
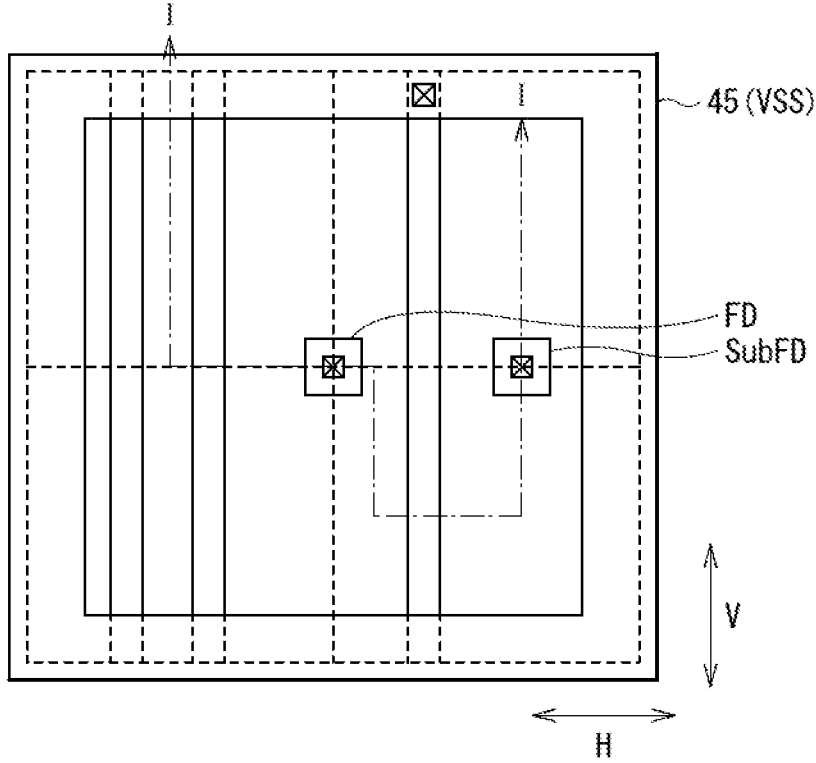
FIG. 10 is a schematic diagram illustrating an example of a wiring layout of the second intermediate wiring layer and an upper wiring layer in the second substrate illustrated in FIG. 1.
Figure 11:
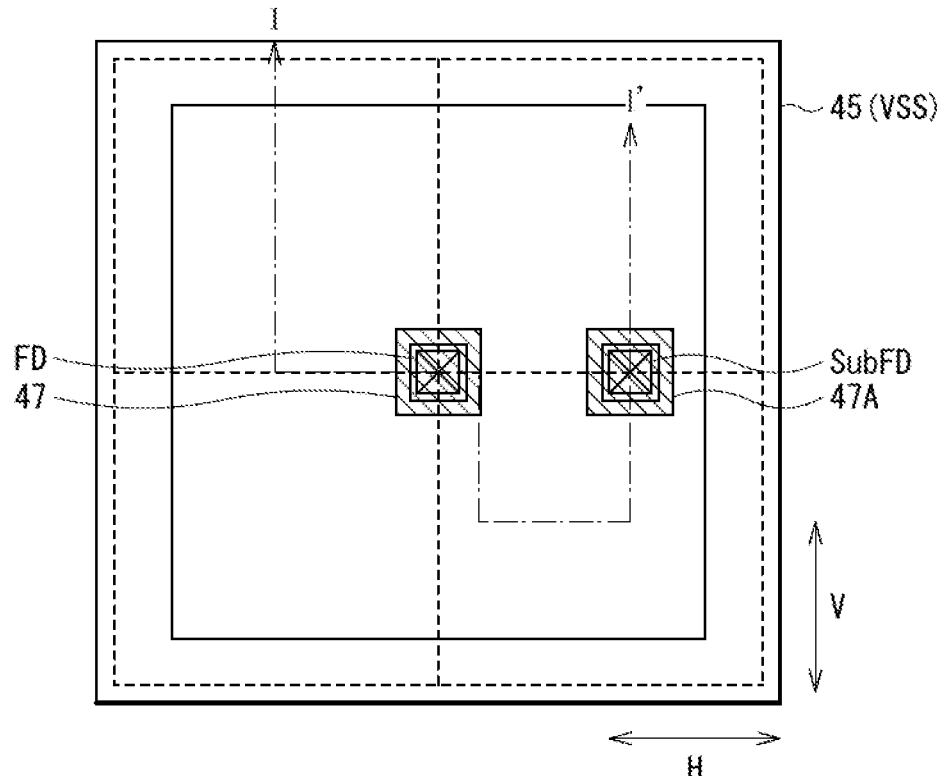
FIG. 11 is a schematic diagram illustrating an example of a wiring layout of the upper wiring layer and a pad electrode in the second substrate illustrated in FIG. 1.

FIG. 1 schematically illustrates an example of a cross-sectional configuration of an imaging device (imaging device 1) according to a first embodiment of the present disclosure in the vertical direction. FIG. 2 illustrates an example of an equivalent circuit of the imaging device 1 illustrated in FIG. 1. FIG. 3 illustrates another example of the equivalent circuit of the imaging device 1 illustrated in FIG. 1. Each of FIGS. 4 to 6 illustrates an example of a wiring layout of the imaging device 1 illustrated in FIG. 1 on a first substrate 100 side. Each of FIGS. 7 to 11 illustrates an example of a wiring layout of the imaging device 1 illustrated in FIG. 1 on a second substrate 200 side. It is to be noted that FIG. 1 illustrates a cross section of the imaging device 1 taken along the I-I' line illustrated in each of FIGS. 4 to 11. The imaging device 1 includes two substrates (the first substrate 100 and the second substrate 200). The imaging device 1 is an imaging device having a three-dimensional structure in which the first substrate 100 and the second substrate 200 are stacked.

The first substrate 100 includes a semiconductor substrate 10 and a wiring layer 30. The semiconductor substrate 10 has a first surface 10A and a second surface 10B that are opposed to each other. The wiring layer 30 is provided on the first surface 10A of the semiconductor substrate 10. The second substrate 200 includes a semiconductor substrate 20 and a wiring layer 40. The semiconductor substrate 20 has a first surface 20A and a second surface 20B that are opposed to each other. The wiring layer 40 is provided on the first surface 20A of the semiconductor substrate 10. In the imaging device 1, the first substrate 100 and the second substrate 200 are stacked with the wiring layer 30 and the wiring layer 40 interposed in between. The wiring layer 30 is provided on the first surface 10A of the semiconductor substrate 10. The wiring layer 40 is provided on the first surface 20A of the semiconductor substrate 20. This semiconductor substrate 10 corresponds to a specific example of a "first semiconductor substrate" according to the present disclosure. The first surface 10A corresponds to a specific example of a "first surface" according to the present disclosure and the second surface 10B corresponds to a specific example of a "second surface" according to the present disclosure. The semiconductor substrate 20 corresponds to a specific example of a "second semiconductor substrate" according to the present disclosure. The first surface 20A corresponds to a specific example of a "third surface" according to the present disclosure and the second surface 20B corresponds to a specific example of a "fourth surface" according to the present disclosure. The wiring layer 30 corresponds to a specific example of a "first wiring layer" according to the present disclosure and the wiring layer 40 corresponds to a specific example of a "second wiring layer" according to the present disclosure.

The first substrate 100 includes a plurality of sensor pixels 11 on the semiconductor substrate 10. Each of the plurality of sensor pixels 11 performs photoelectric conversion. Specifically, the first substrate 100 is provided with a transfer transistor TR along with a photodiode PD (light receiver 12), a floating diffusion FD, and a VSS contact region 13. The second substrate 200 includes a readout circuit 21 on the semiconductor substrate 20. The readout circuit 21 outputs a pixel signal based on electric charge outputted from the sensor pixel 11. The readout circuit 21 includes, for example, four transistors. Specifically, the readout circuit 21 includes an amplification transistor AMP, a selection transistor SEL, a reset transistor RST, and a conversion efficiency switching transistor FDG.

In a case where the transfer transistor TR is turned on, the transfer transistor TR transfers the electric charge of the photodiode PD to the floating diffusion FD.

The reset transistor RST resets the electric potential of the floating diffusion FD to a predetermined electric potential. In a case where the reset transistor RST is turned on, the reset transistor RST resets the electric potential of the floating diffusion FD to a power supply line VDD.

The selection transistor SEL controls a timing at which a pixel signal is outputted from the readout circuit 21.

The amplification transistor AMP generates, as a pixel signal, a signal of a voltage corresponding to the level of electric charge held by the floating diffusion FD. The amplification transistor AMP is included in a source-follower type amplifier and outputs a pixel signal of a voltage corresponding to the level of electric charge generated in the photodiode PD. In a case where the selection transistor SEL is turned on, the amplification transistor AMP amplifies the electric potential of the floating diffusion FD and outputs a voltage corresponding to the electric potential to a logic circuit 25 through a vertical signal line VSL. The logic circuit 25 is described below.

The conversion efficiency switching transistor FDG is used to change the gain of electric charge-voltage conversion by the floating diffusion FD. In general, a pixel signal is small in shooting in a dark place (low illuminance). In a case where electric charge-voltage conversion is performed on the basis of Q=CV, the floating diffusion FD having larger capacitance (FD capacitance C) results in smaller V that is obtained in a case of conversion to a voltage by the amplification transistor AMP. Meanwhile, a bright place (high illuminance) offers a large pixel signal. It is therefore not possible for the floating diffusion FD to receive the electric charge of the photodiode PD unless the FD capacitance C is large. Further, the FD capacitance C has to be large to prevent V from being too large (i.e., to make V small) in a case of conversion to a voltage by the amplification transistor AMP. If these are taken into consideration, the diffusion layer capacitance for the conversion efficiency switching transistor FDG or the diffusion layer capacitance and the wiring capacitance increase in a case where the conversion efficiency switching transistor FDG is turned on. This increases the entire FD capacitance C. Meanwhile, in a case where the conversion efficiency switching transistor FDG is turned off, the whole FD capacitance C becomes small. In this way, switching the conversion efficiency switching transistor FDG on and off enables the FD capacitance C to be variable. This makes it possible to switch the conversion efficiency.

Figure 15:
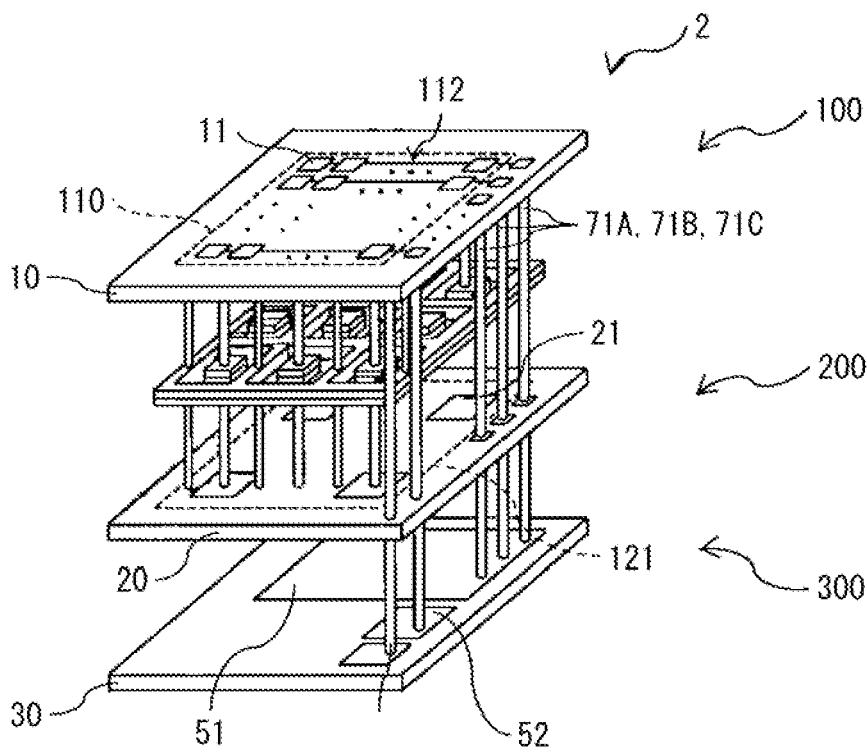
FIG. 15 is a diagram illustrating an exploded perspective configuration example of the imaging device illustrated in FIG. 14.

In the imaging device 1, for example, the plurality of sensor pixels 11 is repeatedly disposed in a pixel region 110 on the first substrate 100 in an array (see, for example, FIG. 15). Specifically, a pixel sharing unit 111 including the plurality of sensor pixels 11 serves as a repeating unit. This pixel sharing unit 111 is repeatedly disposed in an array having a row direction and a column direction. In the present embodiment, the pixel sharing unit 111 includes the four sensor pixels 11 and the four sensor pixels 11 share the one floating diffusion FD. The pixel sharing unit 111 includes the one readout circuit 21 for the four sensor pixels 11. The respective sensor pixels 11 include mutually common components. In FIG. 1 and FIGS. 4 to 11, to distinguish components of the respective sensor pixels 11 from each other, an identification number (1, 2, 3, or 4) is assigned to the end of the symbol of a component of each of the sensor pixels 11. In a case where the components of the respective sensor pixels 11 have to be distinguished from each other, the following assigns an identification number to the end of the symbol of a component of each of the sensor pixels 11. However, in a case where there is no need to distinguish the components of the respective sensor pixels 11 from each other, an identification number at the end of the symbol of a component of each of the sensor pixels 11 is omitted.

For example, the cathode of the photodiode PD is electrically coupled to the source of the transfer transistor TR and the anode of the photodiode PD is electrically coupled to a reference potential line (e.g., ground) in each of the sensor pixels 11. The drain of the transfer transistor TR is electrically coupled to the floating diffusion FD and the gate of the transfer transistor TR is electrically coupled, for example, to a vertical drive circuit 25a described below.

The floating diffusion FD shared by the four sensor pixels 11 is electrically coupled to the input end of the common readout circuit 21. Specifically, the floating diffusion FD is electrically coupled to the gate of the amplification transistor AMP and the source of the conversion efficiency switching transistor FDG. The drain of the conversion efficiency switching transistor FDG is coupled to the source of the reset transistor RST and the gate of the conversion efficiency switching transistor FDG is coupled to a drive signal line (the FDG of a wiring line 43). The drain of the reset transistor RST is coupled to the power supply line VDD and the gate of the reset transistor RST is coupled to a drive signal line (the RST of the wiring line 43). The gate of the amplification transistor AMP is coupled to the floating diffusion FD, the drain of the amplification transistor AMP is coupled to the power supply line VDD, and the source of the amplification transistor AMP is coupled to the drain of the selection transistor SEL. The source of the selection transistor SEL is coupled to the vertical signal line VSL and the gate of the selection transistor SEL is coupled to a drive signal line (the SEL of the wiring line 43).

It is to be noted that FIG. 2 illustrates an example in which the conversion efficiency switching transistor FDG is coupled to the reset transistor RST in series, but this is not limitative. For example, as illustrated in FIG. 3, the conversion efficiency switching transistor FDG may be coupled to the reset transistor RST in parallel.

In the present embodiment, a capacitance addition wiring line X is further coupled, for example, to the drain of the conversion efficiency switching transistor FDG. Although described in detail below, this capacitance addition wiring line X includes a wiring line on the first substrate 100 side and a wiring line on the second substrate 200 side that are electrically coupled to each other. The capacitance addition wiring line X is coupled, for example, to the drain of the conversion efficiency switching transistor FDG to add capacitance. Specifically, the FD capacitance increases in a case where the conversion efficiency switching transistor FDG is turned on at high illuminance. This decreases the conversion efficiency and makes it possible to handle a high saturation signal amount in the same pixel transistor.

Figure 12:
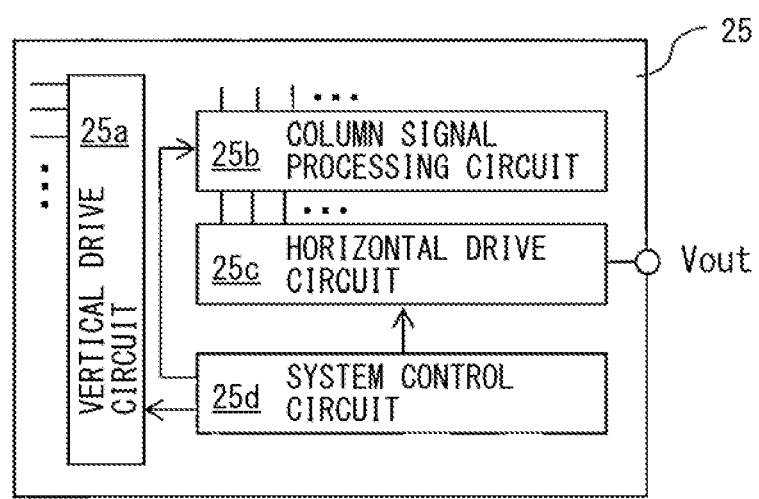
FIG. 12 is a diagram illustrating an example of a functional block of a logic circuit.

The second substrate 200 may further include the logic circuit 25 on the semiconductor substrate 20. The logic circuit 25 controls each of the sensor pixels 11 and each of the readout circuits 21 and processes a pixel signal obtained from the readout circuit 21. The logic circuit 25 includes the vertical drive circuit 25a, a column signal processing circuit 25b, a horizontal drive circuit 25c, and a system control circuit 25d, for example, as illustrated in FIG. 12. The logic circuit 25 outputs an output voltage Vout obtained for each of the sensor pixels 11 to the outside.

The vertical drive circuit 25a selects, for example, the plurality of sensor pixels 11 row by row in order. The vertical drive circuit 25a is electrically coupled, for example, to a plurality of drive wiring lines 112 and selects the plurality of sensor pixels 11 in order row by row by sequentially outputting selection signals to the plurality of drive wiring lines 112.

The column signal processing circuit 25b performs, for example, a correlated double sampling (Correlated Double Sampling: CDS) process on a pixel signal outputted from each of the sensor pixels 11 in a row selected by the vertical drive circuit 25a. The column signal processing circuit 25b performs, for example, the CDS process, thereby extracting the signal level of the pixel signal. The column signal processing circuit 25b holds pixel data corresponding to the amount of light received by each of the sensor pixels 11. The column signal processing circuit 25b is electrically coupled, for example, to the plurality of vertical signal lines VSL and acquires pixel signals from the respective sensor pixels 11 in rows selected by the vertical drive circuit 25a through the plurality of vertical signal lines VSL. The column signal processing circuit 25b includes, for example, ADC (analog-to-digital) for each of the vertical signal lines VSL and converts analog pixel signals acquired through the plurality of vertical signal lines VSL into digital pixel signals.

The horizontal drive circuit 25c sequentially outputs, for example, the pieces of pixel data held by the column signal processing circuit 25b to the outside as the output voltage Vout. The system control circuit 25d controls, for example, the driving of each of the blocks (the vertical drive circuit 25a, the column signal processing circuit 25b, and the horizontal drive circuit 25c) in the logic circuit 25. The booster circuit 52 generates, for example, a power supply potential VDD having predetermined magnitude.

1-2. Specific Configuration of Imaging Device

The semiconductor substrate 10 includes, for example, a silicon substrate. The semiconductor substrate 10 includes the photodiode PD (light receiver 12), the floating diffusion FD and the VSS contact region 13, and the transfer transistor TR, for example, on the first surface 10A side. Further, the semiconductor substrate 10 includes a p well 14 including a p-type semiconductor region. The light receiver 12 includes a semiconductor region of an electrical conduction type (specifically, an n type) different from that of the p well 14. The floating diffusion FD is configured as a semiconductor region of an electrical conduction type (specifically, an n type) different from that of the p well 14. The VSS contact region 13 is configured as a semiconductor region of the same electrical conduction type (specifically, a p type) as that of the p well 14 that has a higher impurity concentration than that of the p well 14. A portion of the VSS contact region 13 is provided in the p well 14. A reference potential line VSS is coupled to the VSS contact region 13. The adjacent sensor pixels 11 are hereby separated from each other electrically by p well 14.

The semiconductor substrate 20 includes, for example, a silicon substrate. The semiconductor substrate 20 is provided with an n-type semiconductor region 22, for example, on the first surface 20A side. The n-type semiconductor region 22 is included in each of the source/drain regions of the amplification transistor AMP, the selection transistor SEL, the reset transistor RST, and the conversion efficiency switching transistor FDG. Further, there are provided a VSS contact region 23 including a p-type semiconductor region and a VDD contact region 24 including an n-type semiconductor region on the first surface 20A side.

The wiring layer 30 has a gate wiring line (e.g., gate wiring line 35; see FIG. 14), a wiring line 31 (lower wiring layer), and a wiring line 32 (upper wiring layer) formed inside an interlayer insulating layer 33. The gate wiring line serves as the gate of the transfer transistor TR. The gate wiring line 35, the wiring line 31, and the wiring line 32 are provided inside the interlayer insulating layer 33 in this order from the first surface 10A side of the semiconductor substrate 10. A plurality of pad electrodes 34 is exposed on a surface of the interlayer insulating layer 33.

For example, the wiring line 31 (lower wiring layer) includes the reference potential line VSS to which a fixed potential is applied. The reference potential line VSS is electrically coupled to the VSS contact region 13 through a via V1. The reference potential line VSS is formed to surround the pixel sharing unit 111 including, for example, the four sensor pixels 11. This reference potential line VSS has a function of a shield that prevents the inter-wiring capacitive coupling of the floating diffusions FD, for example, between the adjacent pixel sharing units 111. The wiring line 31 (lower wiring layer) further includes a wiring line 31A. This wiring line 31A is formed to surround the four transfer transistors TR1, TR2, TR3, and TR4 included in the pixel sharing unit 111. The wiring line 31A is electrically coupled to none of the light receiver 12, the VSS contact region 13, and a transfer transistor FD provided to the semiconductor substrate 10. The wiring line 31A exists in the first substrate 100 in an electrically floating state.

For example, the wiring line 32 (upper wiring layer) includes wiring lines TRG1, TRG2, TRG3, and TRG4 extending in the H direction (row direction). The wiring lines TRG1, TRG2, TRG3, and TRG4 are for respectively sending drive signals to transfer gates TG1, TG2, TR3, and TG4 of the transfer transistors TR1, TR2, TR3, and TR4. The wiring lines TRG1, TRG2, TRG3, and TRG4 are respectively coupled to the transfer gates TG1, TG2, TR3, and TG4 through the wiring line 31 and the vias V1 and V2.

The wiring layer 40 has a gate wiring line 41, a wiring line 42 (lower wiring layer), the wiring line 43 (first intermediate wiring layer), a wiring line 44 (second intermediate wiring layer), and a wiring line 45 (upper wiring layer) formed inside an interlayer insulating layer 46. The gate wiring line 41, the wiring line 42 (lower wiring layer), the wiring line 43 (first intermediate wiring layer), the wiring line 44 (second intermediate wiring layer), and the wiring line 45 (upper wiring layer) serve as the gates of the amplification transistor AMP, the selection transistor SEL, the reset transistor RST, and the conversion efficiency switching transistor FDG. The gate wiring line 41, the wiring line 42, the wiring line 43, the wiring line 44, and the wiring line 45 are provided inside the interlayer insulating layer 46 in this order from the first surface 20A side of the semiconductor substrate 20. A plurality of pad electrodes 47 is exposed on a surface of the interlayer insulating layer 46.

For example, the wiring line 42 (lower wiring layer) and the wiring line 43 (first intermediate wiring layer) include the wiring lines SEL, RST, and FDG (drive signal lines) extending in the H direction (row direction). The wiring line SEL, the wiring line RST, and the wiring line FDG are for respectively sending drive signals to the gate of the selection transistor SEL, the gate of the reset transistor RST, and the gate of the conversion efficiency switching transistor FDG. The wiring lines SEL, RST, and FDG are respectively coupled to the gates of the selection transistor SEL, the reset transistor RST, and the conversion efficiency switching transistor FDG through vias V4 and V5. The wiring line 42 (lower wiring layer) and the wiring line 43 (first intermediate wiring layer) further includes the power supply line VDD and the reference potential line VSS. The power supply line VDD is coupled to the drain of the amplification transistor AMP through the vias V4 and V5. The reference potential line VSS is coupled to the VSS contact region 23 of the semiconductor substrate 20 through the vias V4 and V5.

The wiring line 44 (second intermediate wiring layer) includes, for example, the power supply line VDD, the reference potential line VSS, and the vertical signal line VSL extending in the V direction (column direction). The power supply line VDD is coupled to the power supply line VDD of the wiring line 43 through a via V6 and coupled to the drain of the amplification transistor AMP. The reference potential line VSS is coupled to the reference potential line VSS of the wiring line 43 through the via V6 and coupled to the VSS contact region 23 of the semiconductor substrate 20. The vertical signal line VSL is coupled to the source (Vout) of the selection transistor SEL through the wiring lines 42 and 43 and the vias V4, V5, and V6.

For example, the wiring line 45 (upper wiring layer) includes the reference potential line VSS. The reference potential line VSS is formed to surround the pixel sharing unit 111 including, for example, the four sensor pixels 11 as with the reference potential line VSS of the wiring line 31. The reference potential line VSS is coupled to the reference potential line VSS of the wiring line 44 through a via V7.

The first substrate 100 and the second substrate 200 have the first surface 10A of the semiconductor substrate 10 and the first surface 20A of the semiconductor substrate 20 opposed to each other. The first substrate 100 and the second substrate 200 are bonded together by joining the plurality of pad electrodes 34 and the plurality of pad electrodes 47 exposed from the respective surfaces of the wiring layer 30 and the wiring layer 40 provided on the respective first surfaces 10A and 20A.

The capacitance addition wiring line X described above is formed to include the wiring line 31A and a wiring line 32A of the wiring layer 30 and a wiring line 42A, a wiring line 43A, a wiring line 44A, and a wiring line 45A of the wiring layer 40 formed, for example, above the drain of a conversion efficiency switching transistor FGD. The wiring line 31A and the wiring line 32A are coupled, for example, through the via V2, but each exist in a so-called floating state in which none of elements provided to the first substrate 100 is electrically coupled. The wiring line 42A, the wiring line 43A, the wiring line 44A, and the wiring line 45A are coupled to each other through the vias V5, V6, and V7. The wiring line 42 is electrically coupled to the n-type semiconductor region 22 through the via V4. The n-type semiconductor region 22 serves, for example, as the drain of the conversion efficiency switching transistor FDG. This wiring line 31A and this wiring line 32A each correspond to a specific example of a "first wiring line" according to the present disclosure and the wiring line 42A, the wiring line 43A, the wiring line 44A, and the wiring line 45A each correspond to a specific example of a "second wiring line" according to the present disclosure.

The wiring line 31A extends inside the interlayer insulating layer 33, for example, as illustrated in FIG. 1. The wiring line 31A is formed to surround the four transfer transistors TR1, TR2, TR3, and TR4 included in the pixel sharing unit 111, for example, as illustrated in FIG. 4. The wiring line 31A and the wiring line 32A and the wiring line 42A, the wiring line 43A, the wiring line 44A, and the wiring line 45A are respectively coupled to a pad electrode 34A and a pad electrode 47A, for example, through vias V3 and V8. The pad electrode 34A and the pad electrode 47A are joined to each other. In other words, the wiring line 31A and the wiring line 32A and the wiring line 42A, the wiring line 43A, the wiring line 44A, and the wiring line 45A are electrically coupled. This increases the capacitance of the n-type semiconductor region 22 (sub-floating diffusion SubFD) in a case where the conversion efficiency switching transistor FDG is turned on at high illuminance and increases the signal amount handled in the floating diffusion FD. The n-type semiconductor region 22 (sub-floating diffusion SubFD) serves, for example, as the drain of the conversion efficiency switching transistor FDG. The capacitance addition wiring line X is coupled to the n-type semiconductor region 22 (sub-floating diffusion SubFD).

It is to be noted that FIG. 1 illustrates an example in which the adjacent sensor pixels 11 are electrically separated by the p well 14, but the adjacent sensor pixels 11 mayalso be separated by a pixel separation section including, for example, an insulating film of silicon oxide (SiO) or the like. The pixel separation section is provided, for example, to partition the adjacent sensor pixels 11 from each other and has, for example, a lattice planar shape. The pixel separation section may have, for example, an FTI (Full Trench Isolation) structure in which the pixel separation section extends between the first surface 10A and the second surface 10B of the semiconductor substrate 10. The pixel separation section may have, for example, a DTI (Deep Trench Isolation) structure in which the pixel separation section extends from the first surface 10A to the second surface 10B of the semiconductor substrate 10 and has an end in the semiconductor substrate 10.

1-3. Workings and Effects

The imaging device 1 according to the present embodiment is provided with wiring lines (wiring lines 31A and 32A) that are electrically coupled to none of elements provided to the semiconductor substrate 10 in the wiring layer 30 stacked on the first surface 10A of the semiconductor substrate 10 including the sensor pixel 11. These are electrically coupled to wiring lines (wiring lines 42, 43, 44, and 45) provided inside the wiring layer 40 stacked on the first surface 20A of the semiconductor substrate 20 including the readout circuit 21 and electrically coupled to elements provided to the semiconductor substrate 20. This increases the wiring capacitance. The following describes this.

As described above, to achieve further smaller imaging devices and higher pixel density, imaging devices are developed that each have a three-dimensional structure in which a semiconductor substrate including, for example, a plurality of sensor pixels and a semiconductor substrate including a signal processing circuit that processes a signal obtained by each of the sensor pixels are stacked. Such an imaging device has the photodiode PD, the floating diffusion FD, and a transfer transistor and a pixel transistor other than the transfer transistor formed in different silicon substrates. This increases the area (volume) of the photodiode to increase the saturation electric charge amount and the quantum efficiency. This structure is a structure that is more effective for fine pixels each having a higher area ratio of the pixel transistor region to the pixel size.

In addition, imaging devices are developed that each have a three-dimensional structure in which the photodiode PD, the floating diffusion FD, and the transfer transistor are formed in the first substrate, the pixel transistor other than the transfer transistor is formed in the second substrate, and the logic circuit is formed in the third substrate and these three substrates (the first substrate, the second substrate, and the third substrate) are stacked.

Even in a case of the structure as described above, the channel width and the gate length of the pixel transistor are, however, reduced as the pixel is made finer. This reduces the working range of each of the pixel transistors such as a selection transistor and a reset transistor and consequently reduces the signal charge amount to be handled. In other words, there is an issue with a reduced dynamic range.

Further, the wiring line length of the floating diffusion FD is reduced as the pixel is made finer. The conversion efficiency increases. In other words, the amplitude of the FD potential increases in a case where the same electric charge amount is received. This further reduces the signal charge amount to be handled.

As technology for handling a high saturation signal amount, imaging devices are reported that are each provided with a transistor for capacitance addition which has the floating diffusion FD coupled to an end and has the reset transistor coupled to the other end. This imaging device achieves high conversion efficiency and reduces the influence of noise by turning off the transistor for capacitance addition. In contrast, the imaging device reduces the conversion efficiency by turning on the transistor for capacitance addition in a high illuminance region to add the wiring capacitance, the diffusion layer capacitance, and the oxide film capacitance to the capacitance of the floating diffusion. This makes it possible to handle a high saturation signal amount in the same pixel transistor.

However, even in a case where the technology described above is applied to an imaging device having a three-dimensional structure, a fine pixel has limited area for routing a wiring line for capacitance addition. This limits capacitance to be added and it is difficult to secure sufficient capacitance.

In contrast, in the present embodiment, wiring lines (wiring lines 31A and 32A) that are electrically coupled to none of elements provided to the semiconductor substrate 10 are provided in the wiring layer 30 stacked on the first surface 10A of the semiconductor substrate 10 including the sensor pixel 11. These are electrically coupled, for example, to wiring lines (wiring lines 42, 43, 44, and 45; capacitance addition wiring lines) coupled to the conversion efficiency switching transistor FDG that add capacitance to the conversion efficiency switching transistor FDG, for example, through the pad electrodes 34A and 47A. This couples the capacitance addition wiring line X to the conversion efficiency switching transistor FDG in addition to the wiring layer 40 of the second substrate 200. The capacitance addition wiring line X is routed to the wiring layer 30 of the first substrate 100.

The above allows the imaging device 1 according to the present embodiment to increase the capacitance of the floating diffusion FD in a case where the conversion efficiency switching transistor FDG is turned on. Specifically, the capacitance of the n-type semiconductor region 22 (sub-floating diffusion SubFD) that serves, for example, as the drain of the conversion efficiency switching transistor FDG increases to allow the conversion efficiency to be considerably reduced. The capacitance addition wiring line X is coupled to the n-type semiconductor region 22 (sub-floating diffusion SubFD). This allows the floating diffusion FD to handle a larger signal amount and makes it possible to extend the dynamic range.

In addition, a typical imaging device has no choice but to increase the total number of wiring lines to increase the capacitance of the floating diffusion FD. This leads to a larger number of steps or increasing cost. In contrast, the imaging device 1 according to the present embodiment routes the capacitance addition wiring line X in a wiring layer (the lower wiring layer or the wiring line 31) in the wiring layer 30 on the first substrate 100 side. This makes it possible to increase the capacitance of the floating diffusion FD without increasing the number of steps.

The following describes a second embodiment and modification examples 1 and 2. It is to be noted that the following description denotes the same components as those of the first embodiment described above with the same symbols and the descriptions thereof are omitted as appropriate.

2. MODIFICATION EXAMPLE 1

Figure 13:
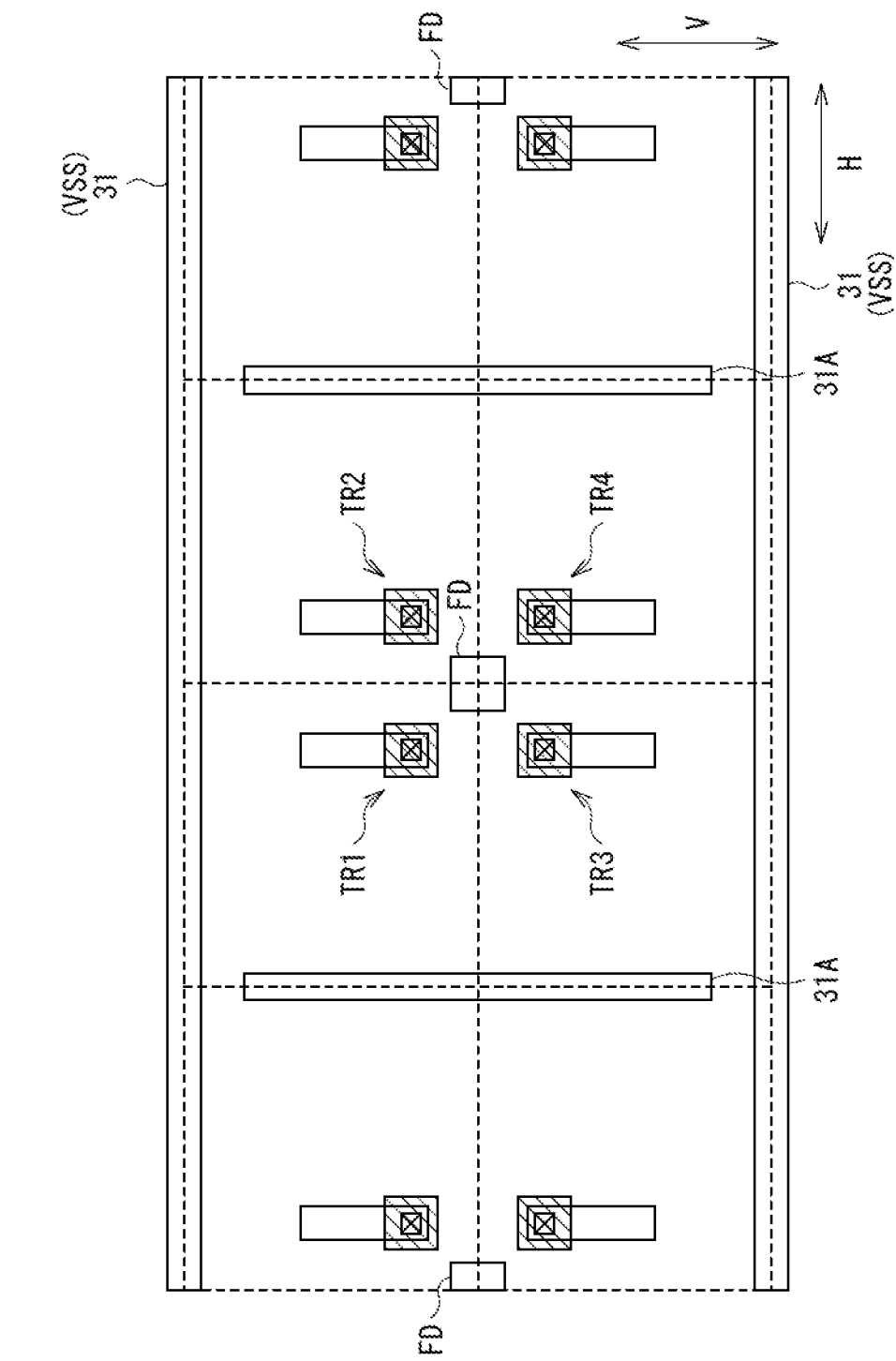
FIG. 13 is a schematic diagram illustrating an example of a wiring layout of an imaging device according to a modification example 1 of the present disclosure.

FIG. 13 schematically illustrates another example of the layout of the lower wiring layer (wiring line 31) in the first substrate 100 of the imaging device 1 as a modification example (modification example 1) of the present disclosure. In the first embodiment described above, the example (FIG. 4) has been described in which the reference potential line VSS surrounds the pixel sharing unit 111 including the four sensor pixels 11, but a reference potential VSS extending in the H direction (column direction) may be omitted and the wiring line 31A included in the capacitance addition wiring line X may be disposed, for example, as illustrated in FIG. 13.

For example, in a case where a pixel is made further finer, the reference potential line VSS of the wiring line 31 that functions as a shield wiring line and the wiring line 31A included in the capacitance addition wiring line X may excessively approach each other and it may be difficult to route the wiring line 31A.

In contrast, in the present modification example, the wiring line 31A included in the capacitance addition wiring line X also serves as a portion of the shield wiring line (the reference potential line VSS of the wiring line 31). In a case where the imaging device 1 is driven in a high conversion efficiency mode at low illuminance, the conversion efficiency switching transistor FDG is turned off and the reset transistor RST is turned on. This fixes the potential of the capacitance addition wiring line X at VDD. This causes the capacitance addition wiring line X (wiring line 31A) having the potential fixed at VDD to shield the region between the pixel sharing units 111 adjacent in the H direction (row direction). This makes it possible to prevent the inter-wiring capacitive coupling of the floating diffusions FD between the adjacent pixel sharing units 111 as in the first embodiment described above.

In addition, the wiring line 31A also serves as a portion of the shield wiring line (the reference potential line VSS of the wiring line 31) to increase the wiring layout efficiency. This makes it possible to route the capacitance addition wiring line X even in a case where the pixels are made further finer. In other words, it is possible to retain the dynamic range.

3. SECOND EMBODIMENT

Figure 14:
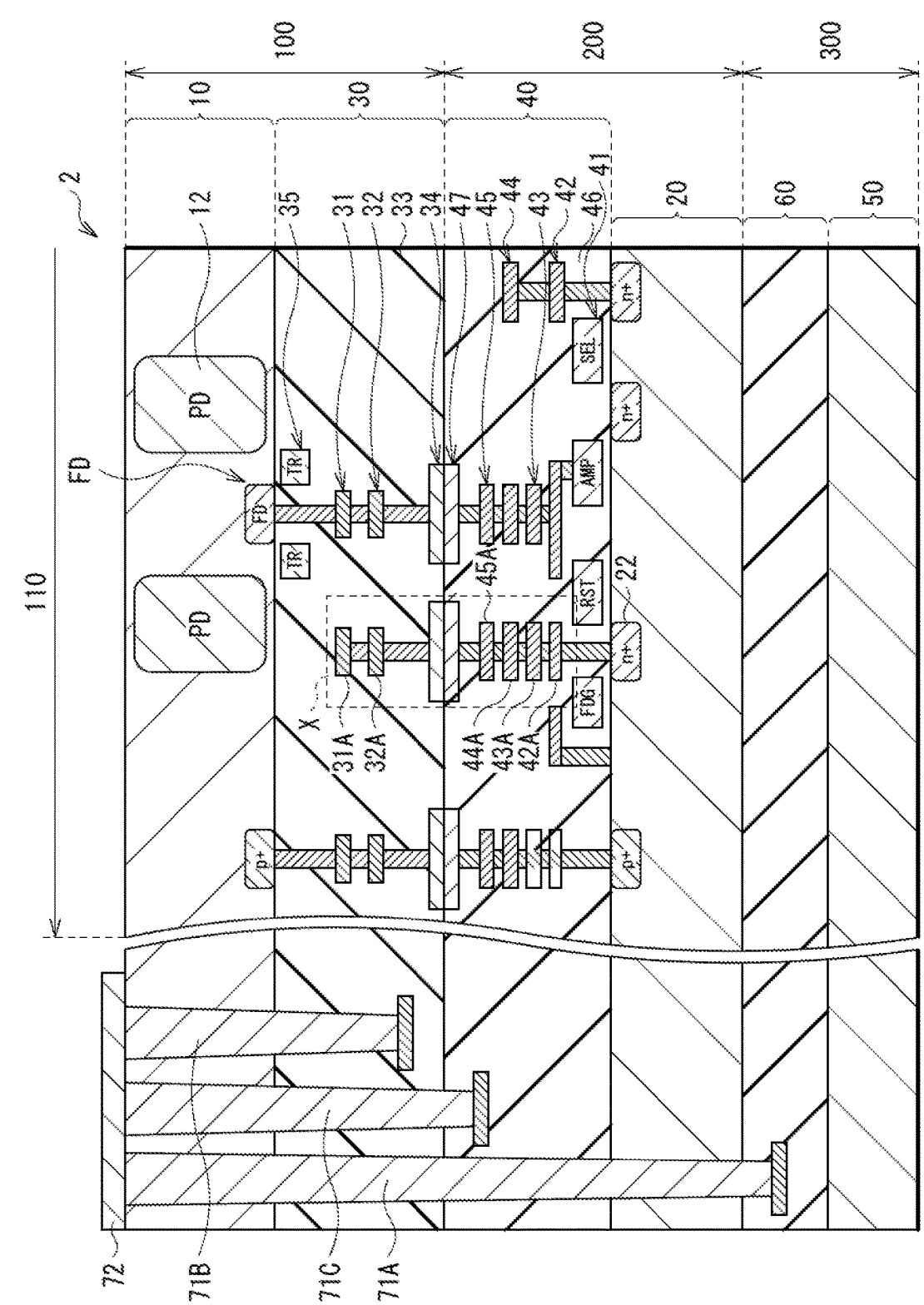
FIG. 14 is a cross-sectional schematic diagram illustrating a configuration of an imaging device according to a second embodiment of the present disclosure in a vertical direction.

FIG. 14 schematically illustrates an example of a cross-sectional configuration of an imaging device (imaging device 2) according to the second embodiment of the present disclosure in the vertical direction. FIG. 15 illustrates an example of a schematic configuration of the imaging device 2 illustrated in FIG. 14. The imaging device 2 includes three substrates (the first substrate 100, the second substrate 200, and a third substrate 300). The imaging device 2 is an imaging device having a three-dimensional structure in which these first substrate 100, second substrate 200, and third substrate 300 are stacked in this order. The imaging device 2 according to the present embodiment is different from that of the first embodiment described above in that a logic circuit (logic circuit 51) is provided to a substrate (third substrate 300) different from that of the readout circuit 21.

The first substrate 100 includes the semiconductor substrate 10 and the wiring layer 30 provided on the first surface 10A of the semiconductor substrate 10 as in the first embodiment described above. The first substrate 100 includes the semiconductor substrate 10 and the plurality of sensor pixels 11 that each performs photoelectric conversion. The plurality of sensor pixels 11 is provided in the pixel region 110 on the first substrate 100 in a matrix. The first substrate 100 includes, for example, the plurality of drive wiring lines 112 extending in the row direction. The plurality of drive wiring lines 112 is electrically coupled to a vertical drive circuit 51a (described below). The plurality of drive wiring lines 112 corresponds, for example, to the wiring lines TRG1, TRG2, TRG3, and TRG4 of the wiring line 32 described above.

The second substrate 200 includes the semiconductor substrate 20 and the wiring layer 40 provided on the first surface 20A of the semiconductor substrate 20 as in the first embodiment described above. The semiconductor substrate 20 includes the one readout circuit 21, for example, for the four sensor pixels 11. The readout circuit 21 outputs a pixel signal based on electric charge outputted from each of the sensor pixels 11. The plurality of readout circuits 21 is provided in matrix in a readout circuit region 121 on the second substrate 200. The wiring layer 40 includes, for example, a plurality of drive wiring lines extending in the row direction and a plurality of vertical signal lines VSL extending in the column direction. The plurality of these drive wiring lines corresponds, for example, to the wiring lines RST, FDG, and SEL of the wiring line 43 described above. The plurality of drive wiring lines provided in the second substrate 200 is electrically coupled to the vertical drive circuit 51a described below. The plurality of vertical signal lines VSL is electrically coupled to a signal processing circuit 51b.

The wiring layer 30 and the wiring layer 40 are provided with the capacitance addition wiring line X formed to include the wiring line 31A and the wiring line 32A of the wiring layer 30 and the wiring line 42A, the wiring line 43A, the wiring line 44A, and the wiring line 45A of the wiring layer 40 provided, for example, above the drain of the conversion efficiency switching transistor FGD as in the first embodiment described above. The wiring layer 30 and the wiring layer 40 are coupled, for example, to the drain (n-type semiconductor region 22) of the conversion efficiency switching transistor FDG.

Figure 16:
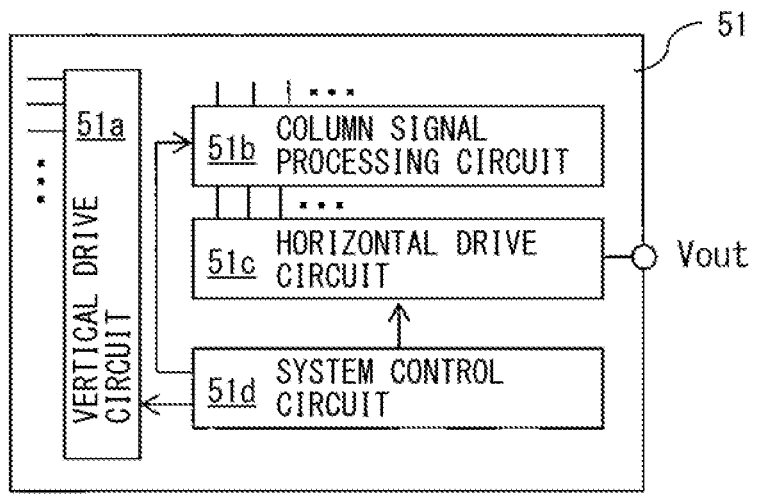
FIG. 16 is a diagram illustrating an example of a functional block of a logic circuit illustrated in FIG. 15.

The third substrate 300 includes a semiconductor substrate 50 and a wiring layer 60. The semiconductor substrate 50 has a first surface 50A and a second surface 50B that are opposed to each other. The wiring layer 60 is provided on the first surface 50A of the semiconductor substrate 50. The semiconductor substrate 50 includes the logic circuit 51 and the booster circuit 52. The logic circuit 51 controls each of the sensor pixels 11 and each of the readout circuits 21 and processes a pixel signal obtained from the readout circuit 21 as with the logic circuit 25 according to the first embodiment described above. The logic circuit 51 includes the vertical drive circuit 51a, a column signal processing circuit 51b, a horizontal drive circuit 51c, and a system control circuit 51d, for example, as illustrated in FIG. 16. The logic circuit 51 outputs the output voltage Vout obtained for each of the sensor pixels 11 to the outside.

The imaging device 2 is provided with a through wiring line 71A around the pixel region 110. For example, the through wiring line 71A is for extracting the output voltage Vout outputted from the logic circuit 51 from the imaging device 2 and supplying the booster circuit 52 with a reference voltage. There are further provided through wiring lines 71B and 71C around the pixel region 110. The through wiring lines 71B and 71C reach the first substrate 100 and the second substrate 200. The through wiring line 71A is electrically coupled to the through wiring lines 71B and 71C through a wiring line 72 provided on a second surface 1B of the semiconductor substrate 10. The output voltage Vout and the boosting potential extracted from the logic circuit 51 are supplied to the first substrate 100 and the second substrate 200 through the through wiring lines 71B and 71C, respectively.

As described above, in the imaging device 2 according to the present embodiment, the logic circuit 51 is provided to the third substrate 300 and the first substrate 100, the second substrate 200, and the third substrate 300 are stacked in this order. The wiring layer 30 of the first substrate 100 and the wiring layer 40 of the second substrate 200 are provided with the capacitance addition wiring line X formed by coupling wiring lines (wiring lines 31A and 32A) that are electrically coupled to none of elements provided to the semiconductor substrate 10 and wiring lines (wiring lines 42, 43, 44, and 45) that are provided in the wiring layer 40 and coupled to the conversion efficiency switching transistor FDG as in the first embodiment described above. This makes it possible to increase the capacitance of the floating diffusion FD without increasing the number of steps and extend the dynamic range as in the first embodiment described above.

4. MODIFICATION EXAMPLE

Figure 17:
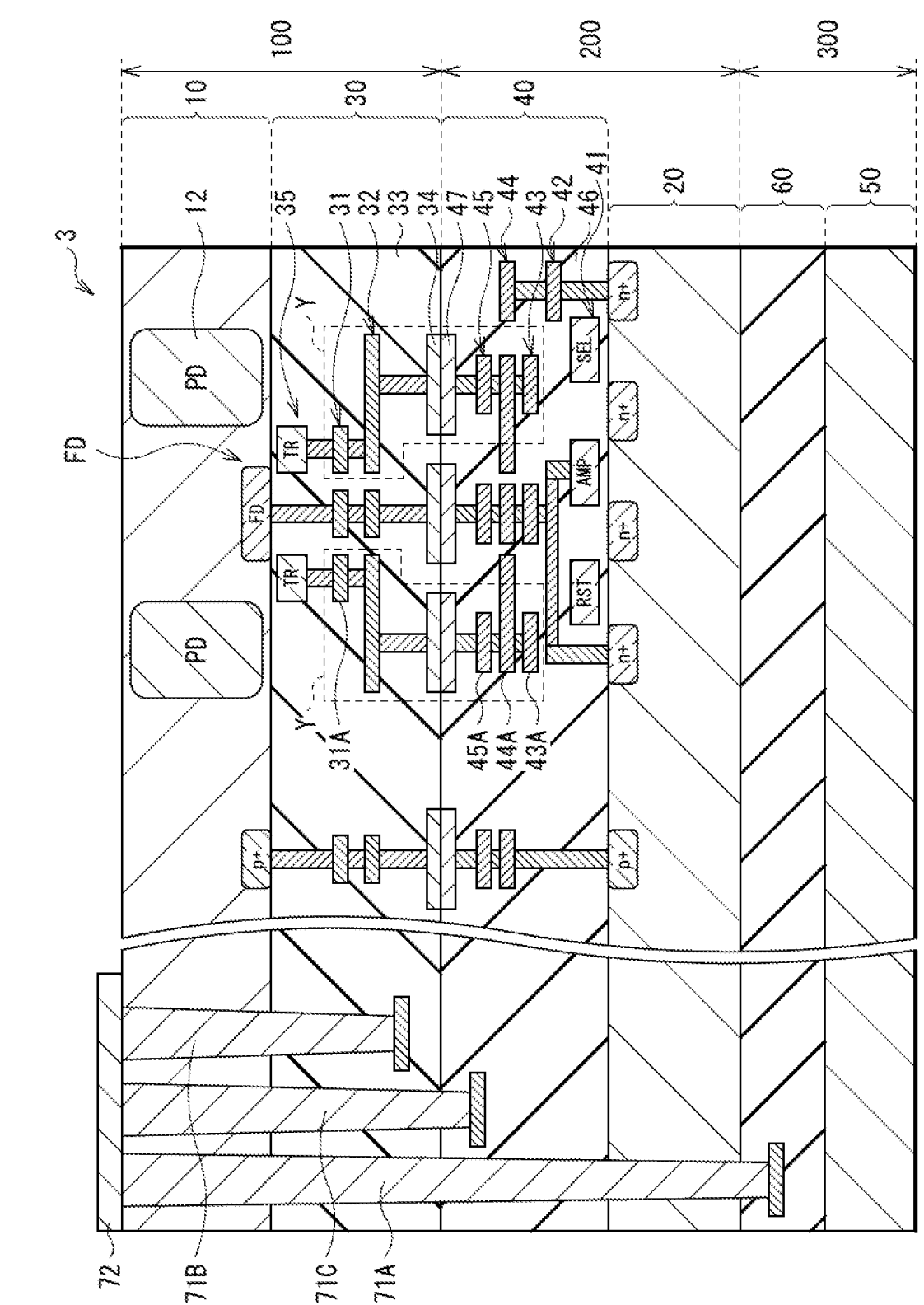
FIG. 17 is a cross-sectional schematic diagram illustrating a configuration of an imaging device according to a modification example 2 of the present disclosure in a vertical direction.

FIG. 17 schematically illustrates an example of a cross-sectional configuration of an imaging device (imaging device 3) according to a modification example (modification example 2) of the present disclosure in the vertical direction. The imaging device 3 is an imaging device having a three-dimensional structure in which the first substrate 100, the second substrate 200, and the third substrate 300 are stacked in this order as in the second embodiment described above.

In the present modification example, for example, the wiring lines TRG1, TRG2, TRG3, and TRG4 provided to the wiring line 32 (upper wiring layer) of the first substrate 100 and a wiring line (e.g., wiring line 44A) existing inside the wiring layer 40 of the second substrate 200 in an electrically floating state are electrically coupled.

In a case where a pixel is made finer, it may be impossible to provide sufficient coupling capacitance between the FD wiring line and the transfer gate wiring line in addition to the issue with a reduced dynamic range described above.

Typical wiring layout technology causes an FD wiring line and a transfer gate wiring line to intentionally extend in parallel and adds coupling capacitance between the FD wiring line and the transfer gate wiring line. This attains an effect of assisting in transferring electric charge from the photodiode PD to the floating diffusion FD owing to a potential difference generated between the photodiode PD and the floating diffusion FD by using the boosting of the FD potential through coupling capacitance with the transfer gate wiring line in a case where the transfer transistor is turned on in transferring electric charge. In a case where a pixel is made finer, the space for routing the FD wiring line and the transfer gate wiring line is limited. It is not thus possible to secure sufficient coupling capacitance and the transfer efficiency of electric charge is reduced.

In contrast, in the present modification example, as described above, for example, the wiring lines TRG1, TRG2, TRG3, and TRG4 provided to the wiring line 32 (upper wiring layer) of the first substrate 100 and wiring lines (e.g., wiring lines 43A, 44A, and 45A) existing inside the wiring layer 40 of the second substrate 200 in an electrically floating state are electrically coupled. This forms wiring lines (e.g., the wiring line 31A, the wiring line TRG1, and the wiring lines 43A, 44A, and 45A; a transfer gate wiring line Y) in the wiring layer 30 and the wiring layer 40 provided between the semiconductor substrate 10 and the semiconductor substrate 20 and forms inter-wiring capacitance between the FD wiring line and the transfer gate wiring line Y. The wiring lines (e.g., the wiring line 31A, the wiring line TRG1, and the wiring lines 43A, 44A, and 45A; the transfer gate wiring line Y) are electrically coupled to the transfer gate TG (e.g., transfer gate TG1) extending in parallel with a wiring line (FD wiring line) that couples the floating diffusion FD provided on the first surface 10A of the semiconductor substrate 10 and the amplification transistor AMP provided on the first surface 20A of the semiconductor substrate 20.

As described above, even in a case where a pixel is made further finer, it is possible to secure a sufficient opposing length between the FD wiring line and the transfer gate wiring line Y. This boosts the FD potential through the transfer gate wiring line Y in transferring electric charge from the light receiver 12 to the floating diffusion FD and makes it possible to increase the transfer efficiency of electric charge. In other words, it is possible to improve the afterimage characteristics.

5. APPLICATION EXAMPLE

Figure 18:
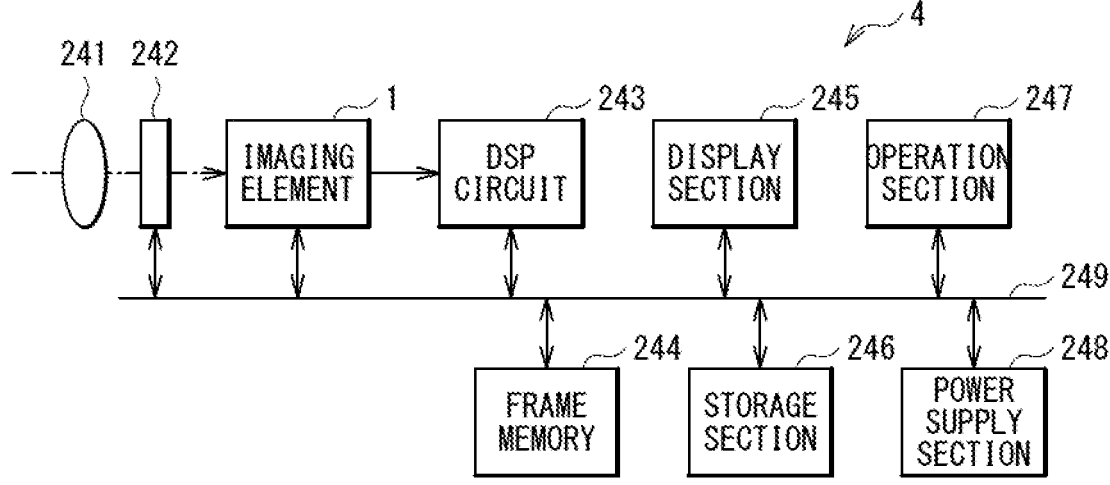
FIG. 18 is a diagram illustrating an example of a schematic configuration of an imaging system including the imaging device according to any of the first and second embodiments and the modification examples 1 and 2 described above.

FIG. 18 illustrates an example of a schematic configuration of an imaging system 4 including the imaging device (e.g., imaging device 1) according to any of the first and second embodiments described above and the modification examples 1 and 2 thereof.

The imaging system 4 is an electronic apparatus including, for example, an imaging device such as a digital still camera or a video camera, a portable terminal device such as a smartphone or a tablet-type terminal, or the like. The imaging system 4 includes, for example, the imaging device 1 according to any of the embodiments described above and the modification examples thereof, a DSP circuit 243, a frame memory 244, a display section 245, a storage section 246, an operation section 247, and a power supply section 248. In the imaging system 4, the imaging device 1 according to any of the embodiments described above and the modification examples thereof, the DSP circuit 243, the frame memory 244, the display section 245, the storage section 246, the operation section 247, and the power supply section 248 are coupled to each other through a bus line 249.

The imaging device 1 according to any of the embodiments described above and the modification examples thereof outputs image data corresponding to incident light. The DSP circuit 243 is a signal processing circuit that processes a signal (image data) outputted from the imaging device 1 according to any of the embodiments described above and the modification examples thereof. The frame memory 244 temporarily holds the image data processed by the DSP circuit 243 in a frame unit. The display section 245 includes, for example, a panel-type display device such as a liquid crystal panel or an organic EL (Electro Luminescence) panel and displays a moving image or a still image captured by the imaging device 1 according to any of the embodiments described above and the modification examples thereof. The storage section 246 records image data of a moving image or a still image captured by the imaging device 1 according to any of the embodiments described above and the modification examples thereof in a recording medium such as a semiconductor memory or a hard disk. The operation section 247 issues an operation instruction for various functions of the imaging system 4 in accordance with an operation by a user. The power supply section 248 appropriately supplies various kinds of power for operation to the imaging device 1 according to any of the embodiments described above and the modification examples thereof, the DSP circuit 243, the frame memory 244, the display section 245, the storage section 246, and the operation section 247 that are supply targets.

Next, an imaging procedure in the imaging system 4 is described.

Figure 19:
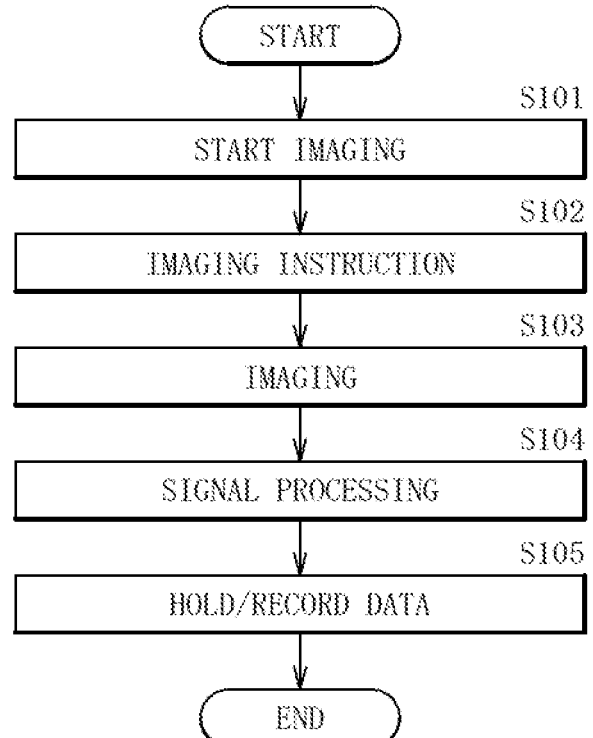
FIG. 19 is a diagram illustrating an example of an imaging procedure in the imaging system in FIG. 18.

FIG. 19 illustrates an example of a flowchart of an imaging operation in the imaging system 4. A user issues an instruction to start imaging by operating the operation section 247 (step S101). The operation section 247 then transmits an imaging instruction to the imaging device 1 (step S102). The imaging device 1 (specifically, a system control circuit) executes imaging in a predetermined imaging scheme upon receiving the imaging instruction (step S103).

The imaging device 1 outputs image data obtained through imaging to the DSP circuit 243. Here, the image data refers to data for all of the pixels of pixel signals generated on the basis of electric charge temporarily held by the floating diffusion FD. The DSP circuit 243 performs predetermined signal processing (e.g., noise reduction processing or the like) on the basis of the image data inputted from the imaging device 1 (step S104). The DSP circuit 243 causes the frame memory 244 to hold the image data subjected to the predetermined signal processing and the frame memory 244 causes the storage section 246 to store the image data (step S105). In this way, the imaging in the imaging system 4 is performed.

In the present application example, the imaging device 1 according to any of the embodiments described above and the modification examples thereof is applied to the imaging system 4. This allows the imaging device 1 to be smaller or higher in definition. This makes it possible to provide the small or high-definition imaging system 4.

6. PRACTICAL APPLICATION EXAMPLES

Practical Application Example 1

The technology (the present technology) according to the present disclosure is applicable to a variety of products. For example, the technology according to the present disclosure may be achieved as a device mounted on any type of mobile body such as an automobile, an electric vehicle, a hybrid electric vehicle, a motorcycle, a bicycle, a personal mobility, an airplane, a drone, a vessel, or a robot.

Figure 20:
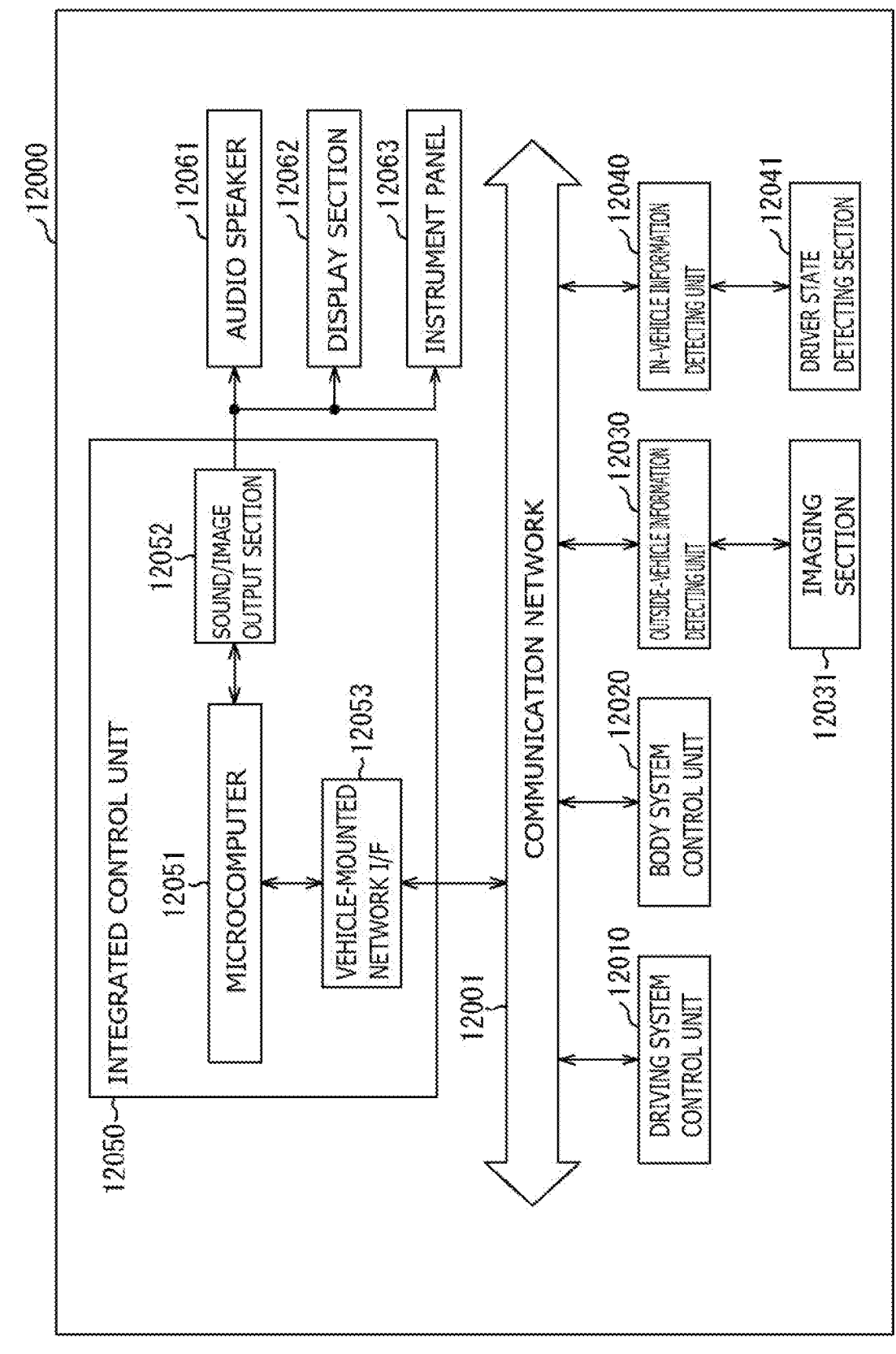
FIG. 20 is a block diagram depicting an example of schematic configuration of a vehicle control system.

FIG. 20 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 20, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 57, an audio speaker 12061, a display section 12062, and an instrument panel 12063 are illustrated as the output device. The display section 12062 may for example, include at least one of an on-board display and a head-up display.

Figure 21:
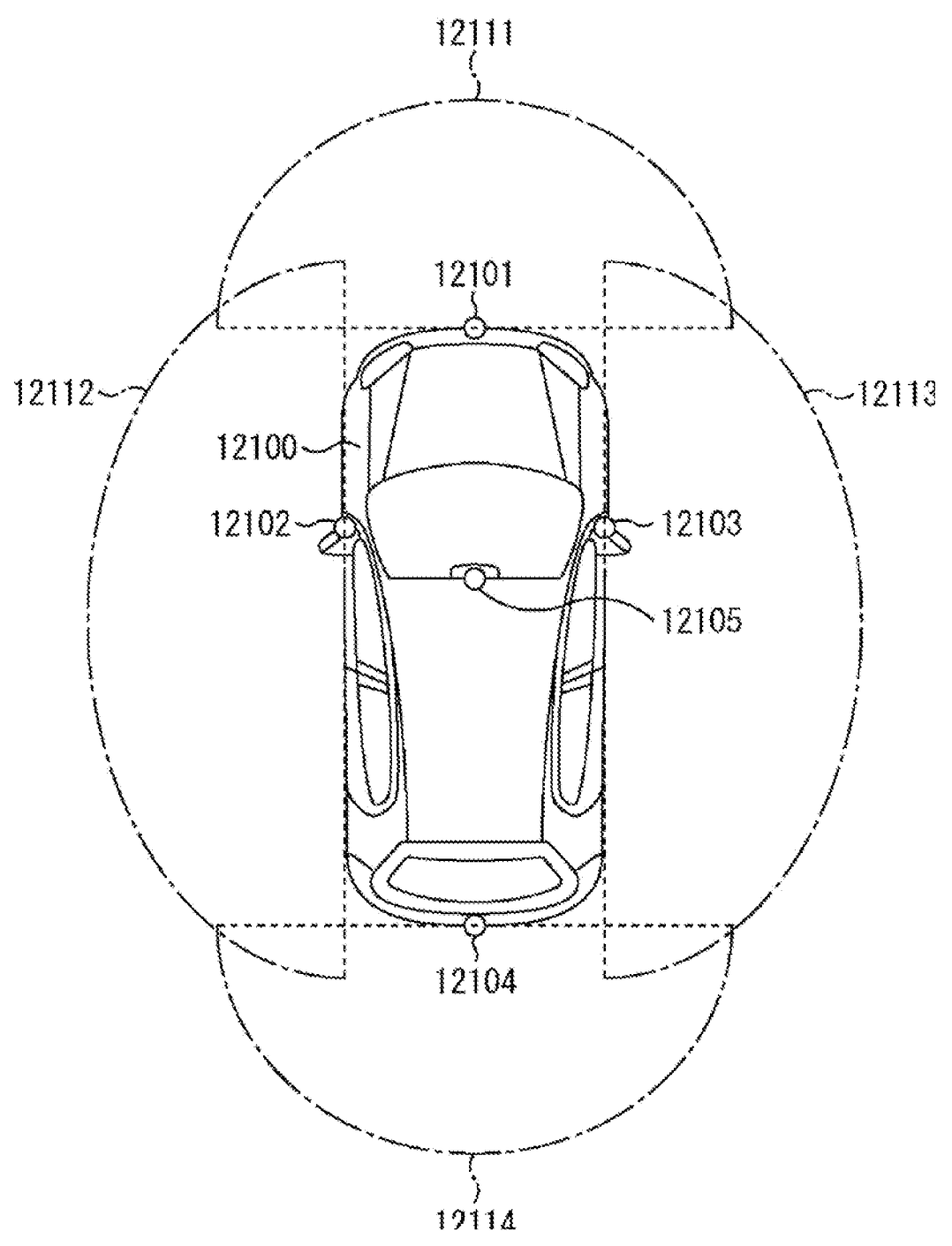
FIG. 21 is a diagram of assistance in explaining an example of installation positions of an outside-vehicle information detecting section and an imaging section.

FIG. 21 is a diagram depicting an example of the installation position of the imaging section 12031.

In FIG. 1022, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 21 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by super-imposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

The above has described the example of the mobile body control system to which the technology according to the present disclosure may be applied. The technology according to the present disclosure may be applied to the imaging section 12031 among the components described above. Specifically, the imaging device 1 according to any of the embodiments described above and the modification examples thereof is applicable to the imaging section 12031. The application of the technology according to the present disclosure to the imaging section 12031 makes it possible to obtain a high-definition shot image with less noise and it is thus possible to perform highly accurate control using the shot image in the mobile body control system.

Practical Application Example 2

Figure 22:
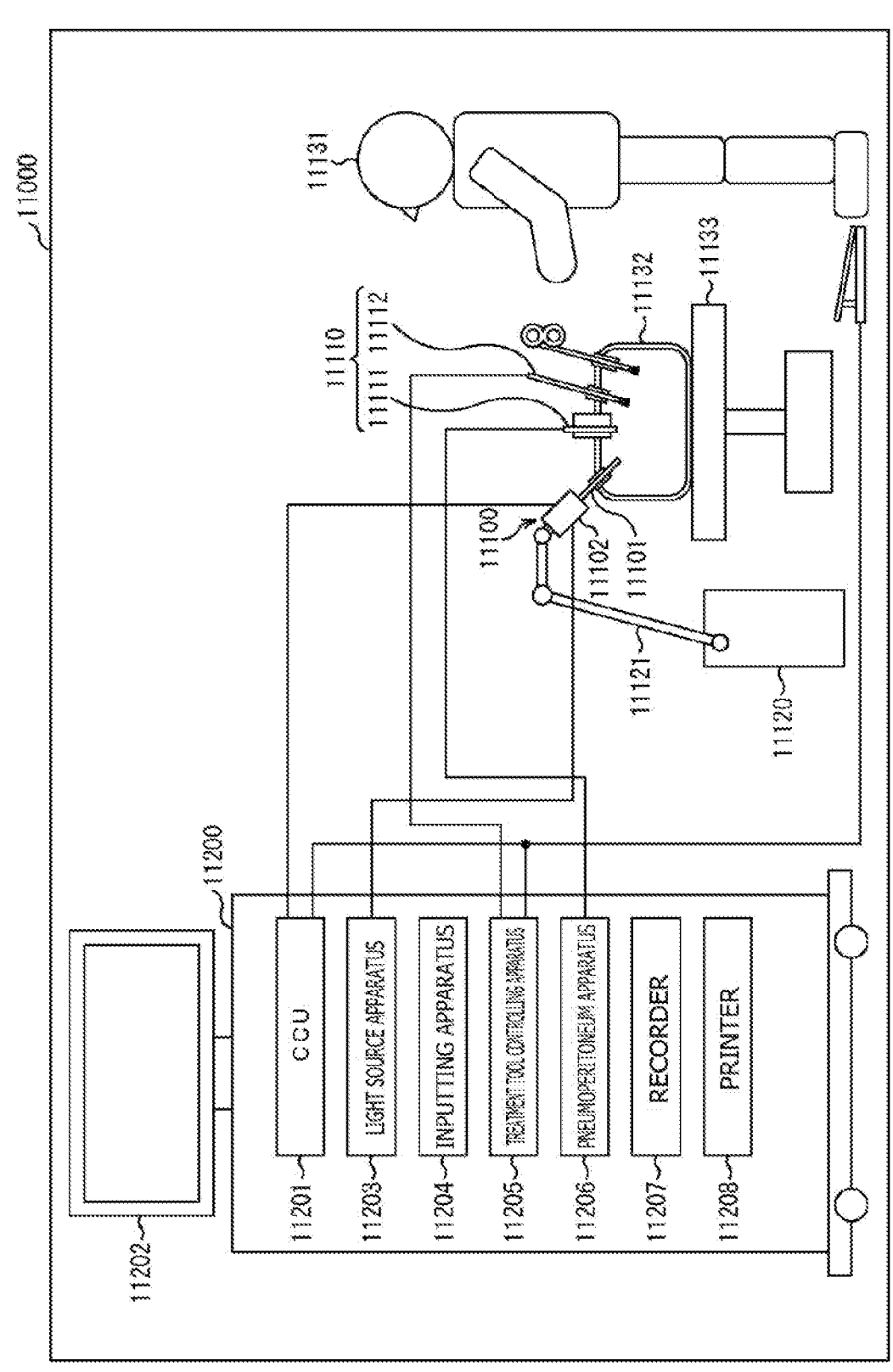
FIG. 22 is a view depicting an example of a schematic configuration of an endoscopic surgery system.

FIG. 22 is a view depicting an example of a schematic configuration of an endoscopic surgery system to which the technology according to an embodiment of the present disclosure (present technology) can be applied.

In FIG. 22, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 23:
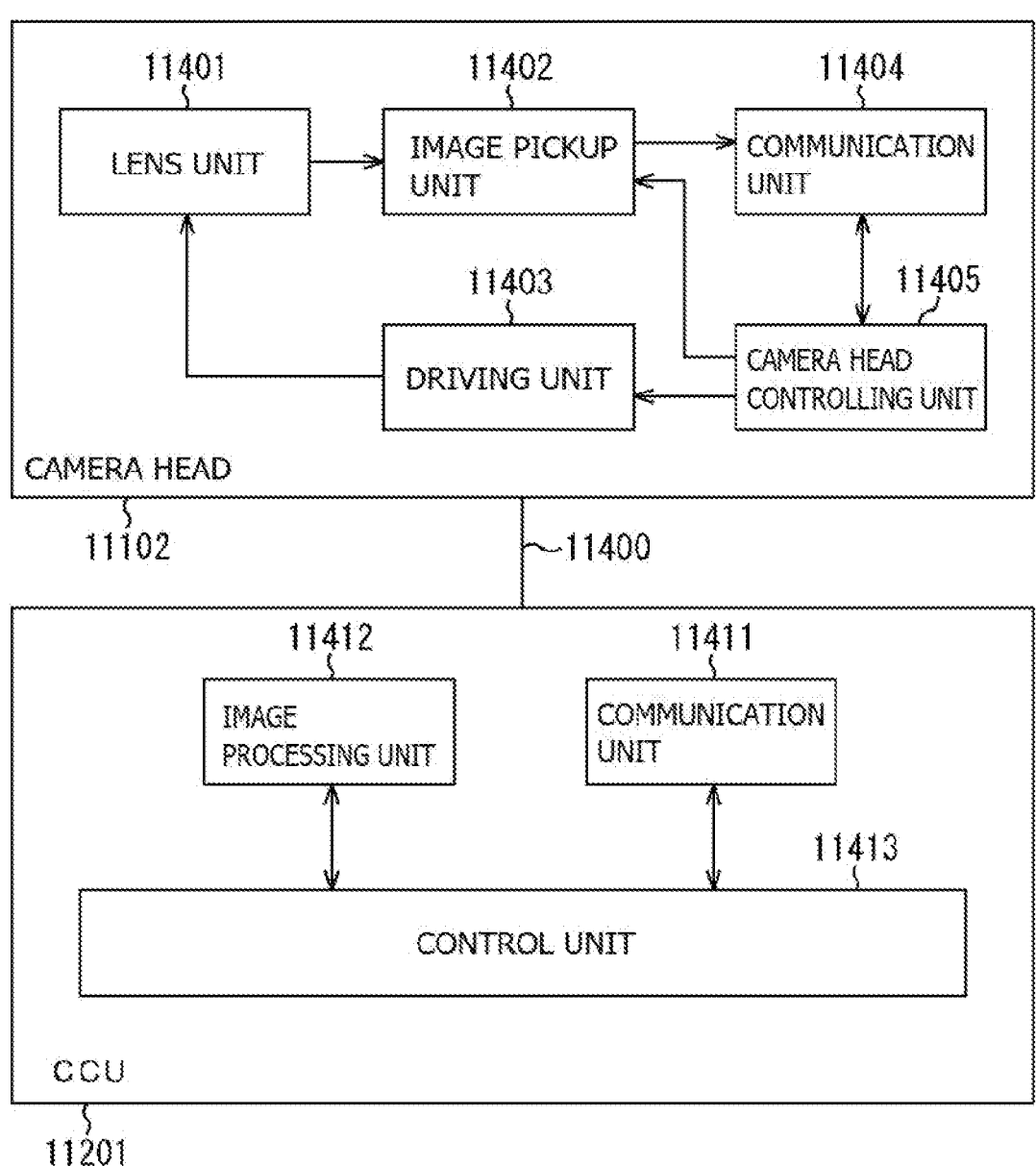
FIG. 23 is a block diagram depicting an example of a functional configuration of a camera head and a camera control unit (CCU).

FIG. 23 is a block diagram depicting an example of a functional configuration of the camera head 11102 and the CCU 11201 depicted in FIG. 22.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

The above has described the example of the endoscopic surgery system to which the technology according to the present disclosure may be applied. The technology according to the present disclosure may be favorably applied to the image pickup unit 11402 provided to the camera head 11102 of the endoscope 11100 among the components described above. The application of the technology according to the present disclosure to the image pickup unit 11402 makes it possible to achieve the downsizing or higher definition of the image pickup unit 11402 and it is thus possible to provide the small or high-definition endoscope 11100.

Although the present disclosure has been described above with reference to the first and second embodiments, the modification examples 1 and 2 thereof, the application example, and the practical application examples, the present disclosure is not limited to the embodiment and the like described above. A variety of modifications are possible.

It is to be noted that the effects described herein are merely illustrative. The effects according to the present disclosure are not limited to the effects described herein. The present disclosure may have effects other than the effects described herein.

It is to be noted that the present disclosure may also have configurations as follows. According to the present technology having the following configurations, the first wiring line and the second wiring line are provided inside the wiring layers formed on the respective opposed surfaces of the first semiconductor substrate including the sensor pixel and the second semiconductor substrate including the readout circuit. This increases the wiring capacitance and makes it possible to extend the dynamic range. One of the first wiring line and the second wiring line is in the electrically floating state. The other of the first wiring line and the second wiring line is electrically coupled to the transistor provided to the first semiconductor substrate or the second semiconductor substrate. The first wiring line and the second wiring line are electrically coupled to each other.

(1)

An imaging device including:

a first semiconductor substrate having a first surface and a second surface and including a sensor pixel that performs photoelectric conversion;

a second semiconductor substrate having a fourth surface and a third surface and including a readout circuit that outputs a pixel signal based on electric charge outputted from the sensor pixel, the second semiconductor substrate being stacked on the first semiconductor substrate with the first surface and the third surface opposed to each other; and a wiring layer provided between the first semiconductor substrate and the second semiconductor substrate and including a first wiring line and a second wiring line that are electrically coupled to each other, one of the first wiring line and the second wiring line being in an electrically floating state while another of the first wiring line and the second wiring line is electrically coupled to a transistor provided to the first semiconductor substrate or the second semiconductor substrate.

(2)

The imaging device according to (1), in which the wiring layer includes a first wiring layer provided on the first surface of the first semiconductor substrate and a second wiring layer provided on the third surface of the second semiconductor substrate, the first wiring line is provided inside the first wiring layer and is in an electrically floating state in the first wiring layer, and the second wiring line is provided inside the second wiring layer and is electrically coupled to the transistor provided to the second semiconductor substrate.

(3)

The imaging device according to (2), in which the first wiring line is not electrically coupled to the transistor provided to the first semiconductor substrate.

(4)

The imaging device according to (1), in which the wiring layer includes a first wiring layer provided on the first surface of the first semiconductor substrate and a second wiring layer provided on the third surface of the second semiconductor substrate, the first wiring line is provided inside the second wiring layer and is in an electrically floating state in the second wiring layer, and the second wiring line is provided inside the first wiring layer and is electrically coupled to the transistor provided to the first semiconductor substrate.

(5)

The imaging device according to (4), in which the first wiring line is not electrically coupled to the transistor provided to the second semiconductor substrate.

(6)

The imaging device according to any one of (1) to (5), in which the sensor pixel includes a light receiver, a transfer transistor, and a floating diffusion, the transfer transistor being electrically coupled to the light receiver, the floating diffusion temporarily holding electric charge outputted from the light receiver through the transfer transistor, and the readout circuit includes a reset transistor, an amplification transistor, a selection transistor, and a conversion efficiency switching transistor, the reset transistor resetting a potential of the floating diffusion to a predetermined position, the amplification transistor generating a signal of a voltage as the pixel signal, the voltage corresponding to a level of the electric charge held by the floating diffusion, the selection transistor controlling a timing at which the pixel signal is outputted from the amplification transistor, the conversion efficiency switching transistor changing electric charge-voltage conversion efficiency at the floating diffusion.

(7)

The imaging device according to (6), in which the other of the first wiring line and the second wiring line is electrically coupled to the conversion efficiency switching transistor.

(8)

The imaging device according to (6), in which the other of the first wiring line and the second wiring line is electrically coupled to the transfer transistor.

(9)

The imaging device according to any one of (2) to (8), in which the first wiring layer and the second wiring layer each include a plurality of pad electrodes that is exposed from a surface, and the first wiring layer and the second wiring layer are bonded together by joining the plurality of pad electrodes to each other.

(10)

The imaging device according to (9), in which the first wiring line and the second wiring line are electrically coupled to a coupling wiring line provided in the first wiring layer and the second wiring layer through the pad electrodes exposed from the respective surfaces of the first wiring layer and the second wiring layer.

(11)

The imaging device according to any one of (6) to (10), the first semiconductor substrate includes the light receiver, the transfer transistor, and the floating diffusion for each of the sensor pixels.

(12)

The imaging device according to any one of (6) to (10), in which the first semiconductor substrate includes the light receiver and the transfer transistor for each of the sensor pixels and shares the floating diffusion between a plurality of the sensor pixels.

(13)

The imaging device according to (12), in which the first semiconductor substrate includes a plurality of pixel sharing units each including a plurality of the sensor pixels that shares the one floating diffusion, and the first wiring line and the second wiring line are disposed between the adjacent pixel sharing units.

(14)

The imaging device according to (13), in which fixed potentials are applied to the first wiring line and the second wiring line.

(15)

The imaging device according to any one of (2) to (14), further including a third substrate including a signal processing circuit on a third semiconductor substrate, the signal processing circuit processing the pixel signal, in which a first substrate, a second substrate, and the third substrate are stacked in this order, the first substrate including the first semiconductor substrate and the first wiring layer, the second substrate including the second semiconductor substrate and the second wiring layer.

(16)

An electronic apparatus including an imaging device including a first semiconductor substrate having a first surface and a second surface and including a sensor pixel that performs photoelectric conversion, a second semiconductor substrate having a fourth surface and a third surface and including a readout circuit that outputs a pixel signal based on electric charge outputted from the sensor pixel, the second semiconductor substrate being stacked on the first semiconductor substrate with the first surface and the third surface opposed to each other, and a wiring layer provided between the first semiconductor substrate and the second semiconductor substrate and including a first wiring line and a second wiring line that are electrically coupled to each other, one of the first wiring line and the second wiring line being in an electrically floating state while another of the first wiring line and the second wiring line is electrically coupled to a transistor provided to the first semiconductor substrate or the second semiconductor substrate.

This application claims the priority on the basis of Japanese Patent Application No. 2019-216511 filed with Japan Patent Office on Nov. 29, 2019, the entire contents of which are incorporated in this application by reference.

It should be understood by those skilled in the art that various modifications, combinations, sub-combinations, and alterations may occur depending on design requirements and other factors insofar as they are within the scope of the appended claims or the equivalents thereof.

What is claimed is:

1. An imaging device, comprising:
a first substrate, including:
    a sensor pixel that performs photoelectric conversion, wherein the sensor pixel includes a floating diffusion;
a second substrate, including:
    a first transistor, wherein the first transistor is one of a plurality of transistors that are included in a readout circuit, and wherein the second substrate is stacked on the first substrate; and
an additional capacitance, wherein the additional capacitance is electrically connected to the first transistor, wherein the additional capacitance overlaps with at least a part of the sensor pixel.

2. The imaging device according to claim 1, wherein the readout circuit includes an efficiency switching transistor, and wherein the additional capacitance is electrically connected to the efficiency switching transistor.

3. The imaging device according to claim 1, wherein the second substrate includes a wiring layer.

4. The imaging device according to claim 3, wherein the additional capacitance is included in the wiring layer of the first substrate.

5. The imaging device according to claim 4, wherein the additional capacitance is formed by two wirings in the wiring layer.

6. The imaging device according to claim 4, the second substrate further including an n-type semiconductor region, wherein the additional capacitance is coupled to the n-type semiconductor region.

7. The imaging device according to claim 6, wherein the readout circuit includes an efficiency switching transistor, and wherein the n-type semiconductor region serves as a drain of the efficiency switching transistor.

8. The imaging device according to claim 3, wherein the first substrate includes a wiring layer.

9. The imaging device according to claim 8, wherein a first wiring line of the additional capacitance is included in the wiring layer of the first substrate, and wherein a second wiring line of the additional capacitance is included in the wiring layer of the second substrate.

10. The imaging device according to claim 9, wherein the first wiring line is coupled to a pad electrode of the first substrate, wherein the second wiring line is coupled to a pad electrode of the second substrate, and wherein the pad electrode of the first substrate is joined to the pad electrode of the second substrate.

11. The imaging device according to claim 10 the second substrate further including an n-type semiconductor region, wherein the readout circuit includes an efficiency switching transistor, and wherein the additional capacitance is coupled to the n-type semiconductor region.

12. The imaging device according to claim 11, wherein the n-type semiconductor region serves as a drain of the efficiency switching transistor.

13. An imaging device, comprising:
a first substrate, including:
    a sensor pixel that performs photoelectric conversion, wherein the sensor pixel includes a floating diffusion;
a second substrate, including:
    a first transistor, wherein the first transistor is one of a plurality of transistors that are included in a readout circuit, and wherein the second substrate is stacked on the first substrate; and
an additional capacitance, wherein the additional capacitance is electrically connected to the first transistor, wherein the readout circuit includes an efficiency switching transistor, and wherein the additional capacitance is electrically connected to the efficiency switching transistor.

14. The imaging device according to claim 13, wherein the additional capacitance overlaps with at least a part of the sensor pixel.

15. An imaging device, comprising:
a first substrate, including:
    a sensor pixel that performs photoelectric conversion, wherein the sensor pixel includes a floating diffusion; and
    a wiring layer;
a second substrate, including:
    a first transistor, wherein the first transistor is one of a plurality of transistors that are included in a readout circuit, and wherein the second substrate is stacked on the first substrate; and
    a wiring layer; and
an additional capacitance, wherein the additional capacitance is electrically connected to the first transistor, and wherein the additional capacitance is included in the wiring layer of the second substrate.

16. The imaging device according to claim 15, wherein the additional capacitance is formed by two wirings in the wiring layer.

17. The imaging device according to claim 15, the second substrate further including an n-type semiconductor region, wherein the additional capacitance is coupled to the n-type semiconductor region.

18. The imaging device according to claim 17, wherein the readout circuit includes an efficiency switching transistor, and wherein the n-type semiconductor region serves as a drain of the efficiency switching transistor.

19. An imaging device, comprising:
a first substrate, including:
    a sensor pixel that performs photoelectric conversion, wherein the sensor pixel includes a floating diffusion; and
    a wiring layer;
a second substrate, including:
    a first transistor, wherein the first transistor is one of a plurality of transistors that are included in a readout circuit, and wherein the second substrate is stacked on the first substrate; and
    a wiring layer; and
an additional capacitance, wherein the additional capacitance is electrically connected to the first transistor, wherein a first wiring line of the additional capacitance is included in the wiring layer of the first substrate, and wherein a second wiring line of the additional capacitance is included in the wiring layer of the second substrate.

20. The imaging device according to claim 19, wherein the first wiring line is coupled to a pad electrode of the first substrate, wherein the second wiring line is coupled to a pad electrode of the second substrate, and wherein the pad electrode of the first substrate is joined to the pad electrode of the second substrate.

* * * * *